United States Patent [19]

Cech et al.

[11] Patent Number: 5,093,246

[45] Date of Patent: Mar. 3, 1992

[54] RNA RIBOZYME POLYMERASES, DEPHOSPHORYLASES, RESTRICTION ENDORIBO-NUCLEASES AND METHODS

[75] Inventors: Thomas R. Cech, Boulder; Arthur J. Zaug, Louisville; Michael D. Been, Boulder, all of Colo.

[73] Assignee: University Patents, Inc., Westport, Conn.

[21] Appl. No.: 562,672

[22] Filed: Aug. 3, 1990

Related U.S. Application Data

[62] Division of Ser. No. 937,327, Dec. 3, 1986, Pat. No. 4,987,071.

[51] Int. Cl.$^5$ .................... C12P 19/34; C12N 15/10; C12N 9/12
[52] U.S. Cl. .................................... 435/91; 435/194; 435/258; 435/320.1; 935/3; 935/16
[58] Field of Search .................. 435/91, 172.3, 193, 435/194, 320.1, 258; 502/167; 935/3, 14, 16; 536/27

[56] References Cited

PUBLICATIONS

Gerlach et al. (1986), Virology, vol. 151, pp. 172-185.
Pharmacia Catalog (1984), p. 35.
BRL Catalog (1983), p. 21.
Guerrier-Takada et al. (1984), Cell, vol. 38, pp. 219-224.
Guerrier-Takada and Altman, "Catalytic Activity of an RNA Molecule Prepared by Transcription in vitro," Science, vol. 223, No. 4631, Jan. 1984, p. 285.
Bass and Cech, Biochemistry, vol. 25, pp. 4473-4477, Aug. 1986.
Bass and Cech, "Specific Interaction Between the Self-Splicing RNA of Tetrahymena and Its Guanosine Substrate: Implications for Biological Catalysis by RNA," Nature, vol. 308, No. 5962, pp. 820-826, 1984.
Been and Cech, "One Binding Site Determines Sequence Specificity of Tetrahymena Pre-rRNA Self-Splicing, Trans-Splicing and RNA Enzyme Activity," Cell, vol. 47, 207-216, Oct. 1986.
Been and Cech, "Sites of Circulation of the Tetrahymena rRNA IVS are Determined by Sequence and Influenced by Position and Secondary Structure," Nucleic Acids Research, vol. 13, No. 23, 1985, p. 8389 (Dec. 9, 1985).
BRL Catalogue, pp. 17, 20 and 21, 1985.
Burke et al., "Role of Conserved Sequence Elements 9L and 2 in Self-Splicing of the Tetrahymena Ribosomal RNA Precursor," Cell, vol. 45, 167-176, Apr. 1986.
Buzayan et al., "Satellite Tobacco Ringspot Virus RNA: A Subset of the RNA Sequence is Sufficient for Autolytic Processing," Proc. Natl. Acad. Sci. USA, vol. 83, pp. 8859-8862, Dec. 1986.
Cech, "A Model for the RNA-Catalyzed Replication of RNA," Proc. Natl. Acad. Sci. USA, vol. 83, pp. 4360-4363, Jun. 1986.
Cech, "Mechanism of Self-Splicing of the Ribosomal RNA Precursor of Tetrahymena," Proceedings of The Robert A. Welch Foundation Conferences on Chemical Research XXIX, Nov. 1985, Houston, TX.

(List continued on next page.)

Primary Examiner—Richard A. Schwartz
Assistant Examiner—Richard M. Lebovitz
Attorney, Agent, or Firm—Lyon & Lyon

[57] ABSTRACT

RNA enzymes or ribozymes can act as endoribonucleases, catalyzing the cleavage of RNA molecules with a sequence specificity of cleavage greater than that of known ribonucleases and approaching that of the DNA restriction endonucleases, thus serving as RNA sequence specific endoribonucleases. An example is a shortened form of the self-splicing ribosomal RNA intervening sequence of Tetrahymena (L-19 IVS RNA). Site-specific mutagenesis of the enzyme active site of the L-19 IVS RNA alters the substrate sequence specificity in a predictable manner, allowing a set of sequence-specific endoribonucleases to be synthesized. Varying conditions allow the ribozyme to act as a polymerase (nucleotidyltransferase), a dephosphorylase (acid phosphatase or phosphotransferase) or a sequence-specific endoribonuclease.

35 Claims, 13 Drawing Sheets

OTHER PUBLICATIONS

Cech, "RNA as an Enzyme," *Scientific American,* vol. 254, No. 11, Nov. 1986.

Cech, "Self-Splicing RNA: Implications for Evolution," *International Review of Cytology,* vol. 93, pp. 4–22, 1985.

Cech, "The Generality of Self-Splicing RNA: Relationship to Nuclear mRNA Splicing," *Cell,* vol. 44, pp. 207–210, 1986.

Cech and Bass, "Biological Catalysis by RNA," *Ann. Rev. Biochem.,* 1986, 55:599–629, Jul. 7, 1986.

Cech et al., "Secondary Structure of the Tetrahymena Ribosomal RNA Intervening Sequence: Structural Homology with Fungal Mitochondrial Intervening Sequences," *Proc. Natl. Acad. Sci USA,* vol. 80, pp. 3903–3907, Jul. 1983.

Davies et al., "Making Ends Meet: A Model for RNA Splicing in Fungal Mitochondria," *Nature,* vol. 300, 23/30 Dec. 1982, p. 719.

Garriga et al., "Mechanism of Recognition of the 5' Splice Site in Self-Splicing Group I Introns," *Nature,* vol. 322, Jul. 1986, p. 86.

Guerrier-Takada et al., "The RNA Moiety of Ribonuclease P is the Catalytic Subunit of the Enzyme," *Cell,* vol. 35, pp. 849–857, Dec. 1983.

Hutchins et al., "Self-cleavage of Plus and Minus RNA Transcripts of Avocado Sunblotch Viroid," *Nucleic Acids Research,* vol. 14, No. 9, 1986, pp. 3627–3640.17.

Inoue et al., "Intermolecular Exon Ligation of the rRNA Precursor of Tetrahymena: Oligonucleotides Can Function as a 5' Exons," *Cell,* vol. 43, 431–437, Dec. 1985.

Inoue et al., "New Reactions of the Ribosomal RNA Precursor of Tetrahymena and the Mechanism of Self-Splicing," *J. Mol. Biol.,* (1986), 189, pp. 143–165.

Inoue and Cech, "Secondary Structure of the Circular Form of the Tetrahymena rRNA Intervening Sequence: A Technique for RNA Structure Analysis Using Chemical Probes and Reverse Transcriptase," *Proc. Natl. Acad. Sci. USA,* vol. 82, pp. 648–652, Feb. 1985.

Kruger et al., "Self-Splicing RNA: Autoexcision and Autocyclization of the Ribosomal RNA Intervening Sequence of Tetrahymena," *Cell,* vol. 31, 147–157, Nov. 1982.

Marsh and Pace, "Ribonuclease P Catalysis Differs from Ribonsomal RNA Self-Splicing," *Science,* vol. 229, No. 4708, Jul. 1985, p. 79.

Michel and Dujon, "Conservation of RNA Secondary Structures in Two Intron Families Including Mitochondrial-, Chloroplast- and Nuclear-Encoded Members," *The EMBO Journal,* vol. 2, No. 1, pp. 33–38, 1983.

Perea and Jacq, "Role of the 5' Hairpin Structure in the Splicing Accuracy of the Fourth Intron of the Yeast Cob-Box Gene," *The EMBO Journal,* vol. 4, No. 12, pp. 3281–3288, 1985.

Price and Cech, "A Coupling of Tetrahymena Ribosomal RNA Splicing to $\beta$-Galactosidase Expression in *Escherichia coli,*" *Science,* vol. 228, pp. 719–722, 1985.

Price et al., *Nuc. Acids Res.,* vol. 13, pp. 1871–1889, Mar. 1985).

Prody et al., "Autolytic Processing of Dimeric Plant Virus Satellite RNA," *Science,* Mar. 1986, pp. 1577–1580.

Sullivan and Cech, "Reversibility of Cyclization of the Tetrahymena rRNA Intervening Sequence: Implication for the Mechanism of Splice Site Choice, *Cell,* vol. 42, 639–648, 1985.

Szostak, "Enzymatic Activity of the Conserved Core of a Group I Self-Splicing Intron," *Nature,* vol. 322, Jul. 1986, pp. 83–86.

Tanner and Cech, "Self-catalyzed Cyclization of the Intervening Sequence RNA of Tetrahymena: Inhibition by Intercalating Dyes, *Nucleic Acids Research,* vol. 13, No. 21, 1985, pp. 7741.

Tanner and Cech, "Self-catalyzed Cyclization of the Intervening Sequence RNA of Tetrahymena: Inhibition by Methidiumpropyl EDTA and Localization of the Major Dye Binding Sites," *Nucleic Acids Research,* vol. 13, No. 21, 1985, p. 7759.

Waring and Davies, "Assessment of a Model for Intron RNA Secondary Structure Relevant to RNA Self-Splicing—A Review," *Gene,* vol. 28, No. 3, Jun. 1984, p. 277.

Waring, "Splice-Site Selection by a Self-Splicing RNA of Tetrahymena," *Nature,* vol. 321, May 1986, p. 133.

Waring et al., "Close Relationship Between Certain Nuclear and Mitochondrial Introns," *J. Mol. Biol.,* (1983) 167, 595–605.

(List continued on next page.)

OTHER PUBLICATIONS

Weaver et al., *Proc. Natl. Acad. Sci.*, vol. 68, pp. 2994–2999, 1971.

Westheimer, "Polyribonucleic Acids and Enzymes," *Nature*, vol. 319, 1986, pp. 534–536.

Zaug et al., "Autocatalytic Cyclization of an Excised Intervening Sequence RNA is a Cleavage-Ligation Reaction," *Nature*, vol. 301, Feb. 1983, p. 578.

Zaug and Cech, "Oligomerization of Intervening Sequence RNA Molecules in the Absence of Proteins," *Science*, vol. 229, pp. 1060–1064, 1985.

Zaug et al., "Reactions of the Intervening Sequence of the Tetrahymena Ribosomal Ribonucleic Acid Precursor: pH Dependence of Cyclization and Site-Specific Hydrolysis," *Biochemistry*, 1985, vol. 24, No. 22, p. 6211.

Zaug and Cech, *Science*, vol. 231, pp. 470–475, Jan., 1986.

Zaug et al., *Science*, vol. 224, pp. 574–578, May 1984.

Zaug and Cech, "The Tetrahymena Intervening Sequence Ribonucleic Acid Enzyme Is a Phosphotransferase and an Acid Phosphatase," *Biochemistry*, 1986, 25, 4478–4482.

Darnell, *Molecular Cell Biology*, 1986, p. 355, 1145–1148.

Garriga and Lambowitz, "RNA Splicing in Neurospora Mitochondria: Self-Splicing of a Mitochondrial Intron In Vitro", *Cell*, vol. 38, 631–641, 1984.

Gerda van der Horst and Tabak, "Self-Splicing of Yeast Mitochondrial Ribosomal and Messenger RNA Precursors", *Cell*, vol. 40, pp. 759–766, 1985.

Ehrenman et al., "Processing of Phage T4 td-encoded RNA is analogous to the eukaryotic group I splicing pathway", *Proc. Natl. Acad. Sci., USA*, vol. 83, pp. 5875–5879, 1986.

Peebles et al., "A Self-Splicing RNA Excises an Intron Lariat", *Cell*, vol. 44, pp. 213–223, 1986.

R. van der Veen et al., "Excised Group II Introns in Yeast Mitochondria are Lariats and Can Be Formed by Self-splicing In Vitro", *Cell*, vol. 44, 225–234, 1986.

Jacquier and Rosbash, "Efficient Trans-splicing of a Yeast Mitochondrial RNA Group II Intron Implicates a Strong 5' Exon-Intron Interaction", *Science*, vol. 234, pp. 1099–1104, 1986.

Zaug and Cech, "Discovery of a New RNA Enzyme", *Abstracts*, Cold Spring Harbor Lab., 1986.

A. D. M. van Mansfeld et al., "Recognition sequence of bacteriophage $_T$X174 gene A protein—An initiator of DNA replication", Nature 288:301, 1980.

Szybalski, "Universal restriction endonucleases: designing novel cleavage specificties by combining adapter oligodeoxynucleotide and enzyme moieties", Gene 40:169, 1985.

Podhajska and Szybalski, "Conversion of the *Fok*I endonuclease to a universal restriction enzyme: cleavage of phage M13mp7 DNA at predetermined sites", Gene 40:175, 1985.

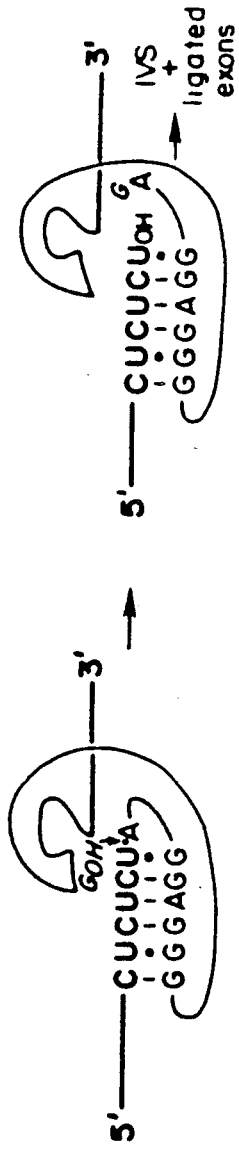
Fig. 1A. Self-splicing
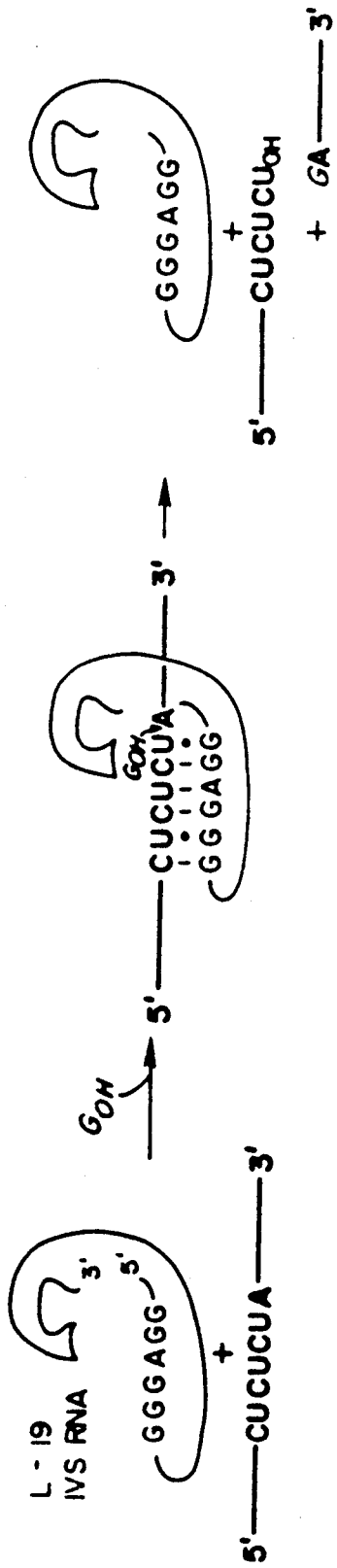
Fig. 1B. RNA "restriction endonuclease"

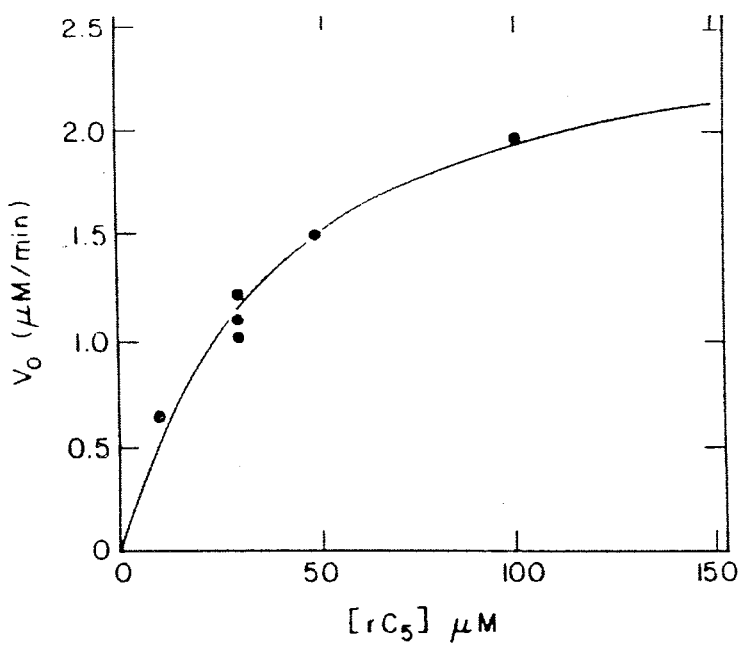

Competitive Inhibition

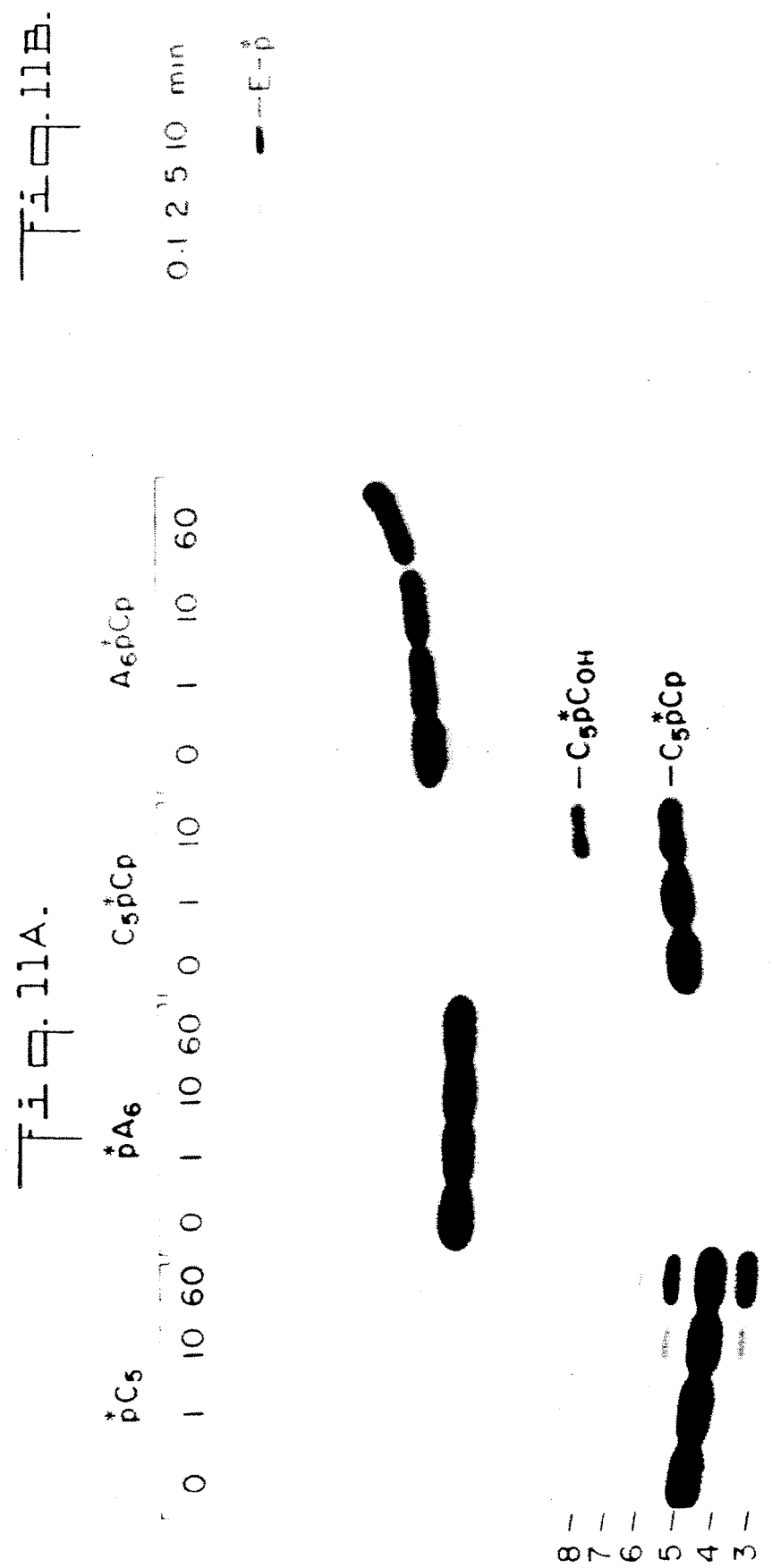

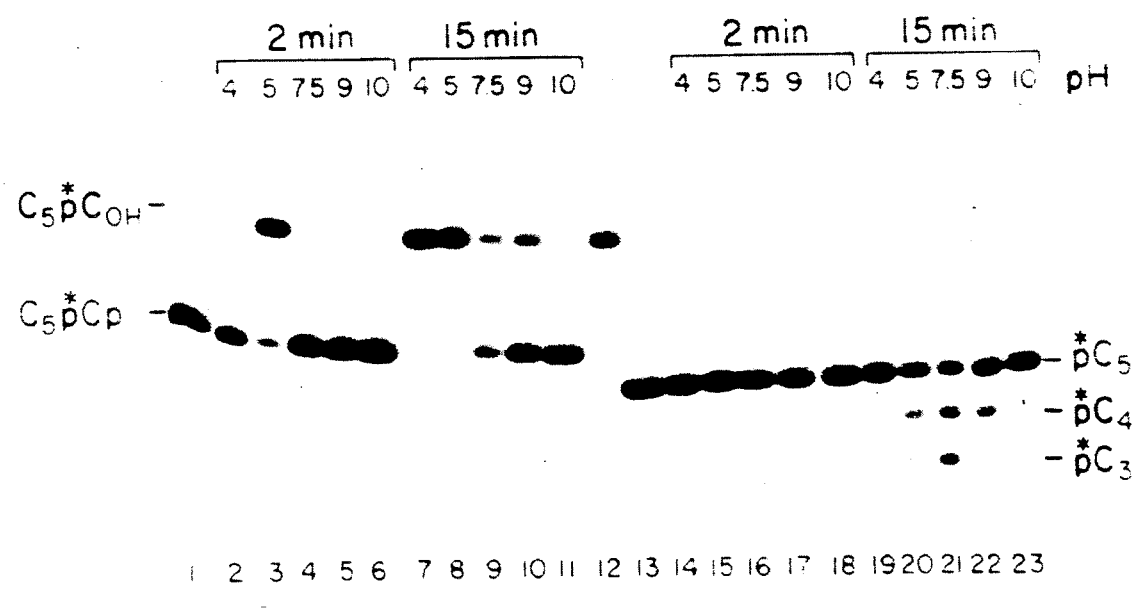
Fig. 12A.
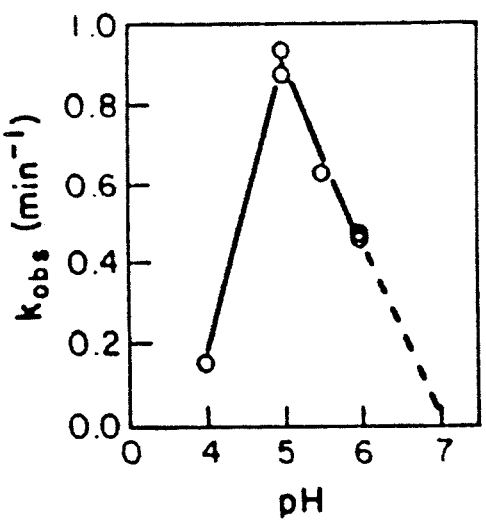
Fig. 12B.
Fig. 12C.

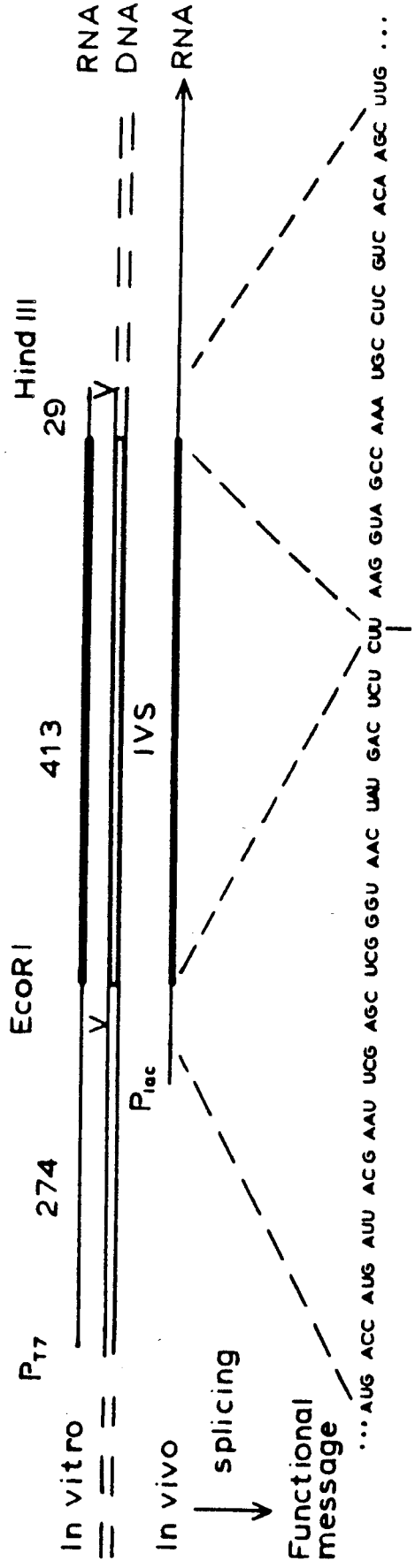

RNA RIBOZYME POLYMERASES, DEPHOSPHORYLASES, RESTRICTION ENDORIBO-NUCLEASES AND METHODS

This is a divisional of Ser. No. 06/937,327, filed on Dec. 3, 1986, which is now U.S. Pat. No. 4,987,071.

This invention concerns compositions of RNA functioning as an RNA enzyme, i.e. a ribozyme in several capacities: dephosphorylase (acid phosphatase and transphosphorylase), ribonucleotidyl transferase (polymerase activity) and sequence-specific endoribonuclease activities.

SUMMARY

It is found that purified ribonucleic acid (RNA) can serve as an enzyme acting on other RNA molecules in vitro (ribozyme) as a: 1) dephosphorylating enzyme catalyzing the removal of 3' terminal phosphate of RNA in a sequence-specific manner, 2) RNA polymerase (nucleotidyl transferase) catalyzing the conversion of oligoribonucleotides to polyribonucleotides, 3) sequence specific endoribonuclease. (This latter activity is also referred to as RNA restriction endonuclease or endoribonuclease activity.)

DESCRIPTION OF THE DRAWINGS

FIG. 1 compares RNA self-splicing (A) to RNA endoribonuclease activity (B).

FIG. 2 shows products of cleavage of a variety of RNA substrates by the RNA endoribonuclease.

FIG. 6 shows the kinetics of conversion of $pC_5$ to larger and smaller oligonucleotides with L-19 IVS RNA.

FIG. 7 shows the enzyme-substrate intermediate of L-19 IVS RNA.

FIG. 11 shows the dephosphorylation of oligo (cytidylic acid) 3-phosphate.

FIG. 12 shows the effect of pH on phosphotransfer and nucleotidyl transfer reactions.

FIG. 16 shows the plasmid construction which produces the L-21 IVS RNA.

DETAILED DESCRIPTION OF THE DRAWINGS

Figure Legends

Figure 3A:
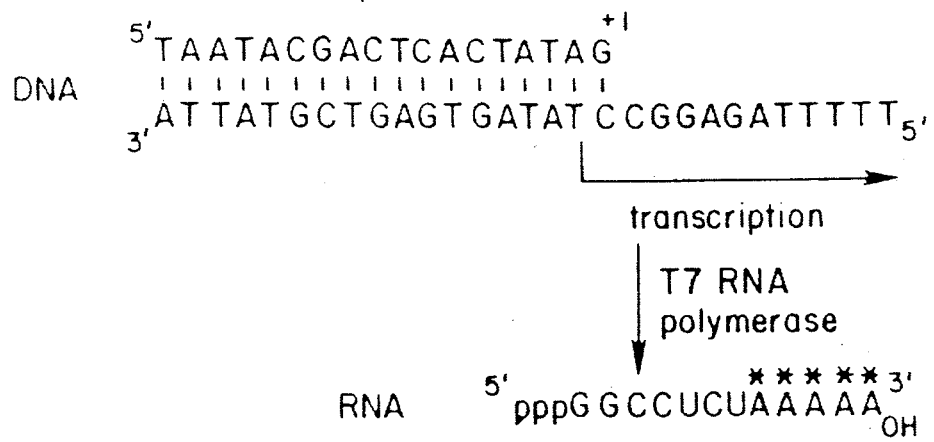
FIG. 3 compares different substrate activity of three variant forms of L-19 IVS ribozyme in 2.5M urea.

FIG. 1 A model for the L-19 IVS RNA acting like an RNA restriction endonuclease by a mechanism that is an intermolecular version of the first step of pre-rRNA self-splicing. Thin letters and lines represent IVS sequences, boldface letters and thick lines represent exon sequences (above) or substrate RNA sequences (below), and the G in italics is a free guanosine nucleotide or nucleoside.

FIG. 2 The L-19 IVS-beta RNA cleaves large RNA substrates with transfer of guanosine. a, Uniformly labeled 0.6 uM (u=micro) pAK105 RNA (508 nt) incubated with 0.2 uM L-19 IVS-beta RNA and 0, 0.1 or 0.5 mM GTP (unlabeled) for 1 h under conditions described below. (M) Mixture of 4 substrate RNAs as molecular weight markers. b, Various tritiated RNA substrates (1 ug each) incubated with 0.2 uM L-19 IVS-beta RNA and 120 uM [alpha-$^{32}$P]GTP for 1 h under the same reaction conditions as a. Autoradiogram reveals [$^{32}$p]GTP-labeled products only. The L-19 IVS-beta RNA also becomes GTP-labeled during the incubation. c, Nucleotide sequence of the cleavage product pAK105(1) determined by the enzymatic method (Donis-Keller, H., (1980) Nucleic Acids Res. 8:3133–3142). Some nucleotides could not be assigned due to presence of a band in the untreated (control) RNA sample. G*, labeled GTP joined to the RNA during the reaction.

Methods: L-19 IVS RNA was synthesized by methods similar to those described previously (Zaug, A. J., and Cech, T. R., (1986) Science 231:470–475), except a different RNA polymerase-template system was used. Plasmid pT7-TT1A3 (which contains a T7 RNA polymerase promoter, a 42 bp 5' exon, the entire 413 bp IVS, and an 82 bp 3' exon) was cleaved with Eco RI and transcribed with bacteriophage T7 RNA polymerase (Davanloo, P., et al. (1984) Proc. Nat'l. Acad. Sci. U.S.A. 81: 2035–2039). The transcripts were incubated further under self-splicing, cyclization, and site-specific hydrolysis conditions to produce L-19 IVS RNA (Zaug, A. J., et al. (1984) Science 224:574–578; Zaug, A. J. and Cech, T. R., (1986) Science 231:470–475). The 3'-terminal guanosine was then removed by periodate oxidation and beta-elimination (Winter, G., et al. (1978) Nucleic Acids Res. 5, 3129–3139) to yield L-19 IVS-beta RNA. Substrate RNAs were produced by T7 RNA polymerase transcription of BamHI-cleaved pAK105 (Mount, S. M., et al. (1983) Cell 33:509–518), XmnI- or ScaI-cleaved pT7-1 (purchased from U.S. Biochemical Corp.), and SnaBI-cleaved pDW27, which encodes M1 RNA (obtained from D. Wahl and N. Pace). Substrate RNAs were incubated with L-19 IVS-beta RNA in 5 mM $MgCl_2$, 10 mM NaCl, 50 mM Tris-HCl, pH 7.5 at 50° C.; in addition, GTP was present at the concentration indicated. Reactions were stopped by the addition of EDTA to a final concentration of 25 mM. Products were analyzed by electrophoresis in 4% polyacrylamide, 8M urea gels and subjected to fluorography (a) or autoradiography (b).

FIG. 3 Three different ribozymes can distinguish between sequences that differ by only one single-base change within the recognition element a, Synthesis of defined oligoribonucleotide substrates by the method of Lowary et al. (Lowary, P., et al. NATO ASI Series A, vol. 110, 69–76 1986). DNA was transcribed with T7 RNA polymerase in the presence of [alpha-$^{32}$P]ATP to produce oligoribonucleotides labeled with $^{32}$P in the positions indicated (*). b, Proposed interactions between the three oligoribonucleotide substrates (top strands, boldface letters) and the active sites of the matched ribozymes (bottom strands). Arrows designate sites of cleavage and guanosine addition c, Cleavage of 3 oligoribonucleotide substrates by wild-type and variant L-19 IVS RNAs, assayed by 20% polyacrylamide, 7M urea gel electrophoresis. (—), untreated substrate. In other pairs of lanes, 1.0 uM $^{32}$p-labeled substrate was incubated with 0.125M ribozyme for 15 min (left lane) or 60 min (right lane) at 50° C. in 10 mM MgCl$_2$, 10 mM NaCl, 50 mM Tris-HCl, pH 7.5, 0.5 mM GTP (unlabeled), 2.5M urea. Because the $^{32}$P is confined to the nucleotides downstream from the cleavage site, only the smaller of the products is apparent. The identity of the GA$_5$ product was confirmed by treatment of the substrate and reaction mixtures with RNase T$_2$ and monitoring the transfer of $^{32}$P to Gp. The band migrating above GA$_5$ in lanes 2 and 3 was not produced consistently and has not been identified.

Methods: Substrates were prepared by transcription of deoxyoligonucleotides synthesized on an Applied Biosystems DNA Synthesizer. The same promoter top strand was used in each transcription. The bottom strand, which contains promoter and template sequences, was varied to obtain the different RNA substrates. The DNA was transcribed with purified phage T7 RNA polymerase (Davanloo, P., et al. (1984) Proc. Nat'l. Acad. Sci. U.S.A. 81:2035-2039) as described (Lowary, P., et al. NATO ASI Series, vol. 110, as above). Variant ribozymes are described by Been and Cech (Been, M. D., et al. (1986) Cell, 47:207-216). The 24C ribozyme was similarly prepared from transcripts of pBG/-3G:24C. The variant ribozymes were not subjected to beta-elimination to remove their 3'-terminal G.

Figure 3B:
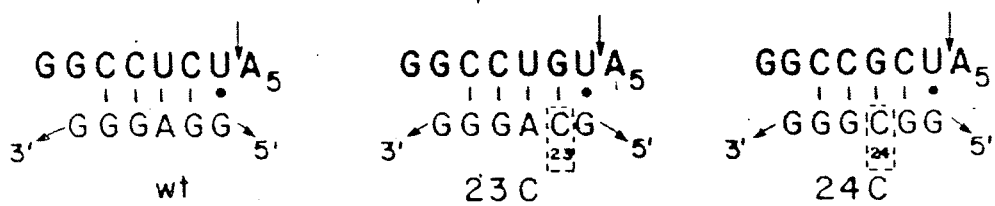

FIG. 4 Kinetic analysis of the RNA endoribonuclease reaction. a, The oligoribonucleotide substrate (2.5 uM) was incubated with wild-type L-19 IVS-beta RNA (0.2 uM) as in FIG. 3, except that urea was omitted. b, Kinetics of cleavage of GGCCCUCUA$_5$ as a function of GTP concentration. RNA substrate concentration was kept constant at 2.5 uM. c, Kinetics of cleavage as a function of RNA substrate concentration, with GTP concentration kept constant at 0.5 mM.

Methods: Products were separated by polyacrylamide gel electrophoresis. With the autoradiogram as a guide, each gel was cut into strips, and the radioactivity in the unreacted substrate and the GA$_5$ product was determined by liquid scintillation counting. The initial velocity of cleavage (Vo) was determined from a semi-logarithmic plot of the fraction of reaction as a function of time. 1/Vo was then plotted as a function of inverse substrate concentration; the graphs are linear least-squares fits to the data points.

FIG. 5 The L-19 IVS RNA catalyzes the cleavage and rejoining of oligoribonucleotide substrates; (A) 10 uM pC$_5$ and (B) 10 uM d-pC$_5$, both with 1.6 uM L-19 IVS RNA; (C) 45 uM pC$_5$ in the absence of L-19 IVS RNA; (D) 45 uM pU$^6$ with 1.6 uM L-19 IVS RNA; (E) 10 uM pC$_5$, (F) 50 uM pC$_5$ and (G) 100 uM pC$_5$, all with 1.6 uM L-19 IVS RNA. Oligonucleotides were 5'-end labeled by treatment with [gamma-$^{32}$P]ATP and polynucleotide kinase; they were diluted with unlabeled oligonucleotide of the same sequence to keep the amount of radioactivity per reaction constant The L-19 IVS RNA was synthesized by transcription and splicing in vitro. Supercoiled pSPTT1A3 DNA (Price, J. V., et al. (1985) Science 228:719) was cut with Eco RI and then transcribed with SP6 RNA polymerase (Butler, E. T., et al. (1982) J. Biol. Chem. 257:5772; Melton, D. A., et al. (1984) Nucleic Acids Res. 12:7035) for 2 hours at 37° C. in a solution of nucleoside triphosphates (0.5 mM each), 6 mM MgCl$_2$, 4 mM spermidine, 10 mM dithiothreitol, 40 mM tris-HCl, pH 7.5, with 100 units of SP6 RNA polymerase per microgram of plasmid DNA. Then NaCl was added to a final concentration of 240 mM and incubation was continued at 37° C. for 30 minutes to promote excision and cyclization of the IVS RNA. Nucleic acids were precipitated with three volumes of ethanol and redissolved in 50 mM CHES, pH 9.0; MgCl$_2$ was added to a final concentration of 20 mM, and the solution was incubated at 42° C. for 1 hour to promote site-specific hydrolysis of the circular IVS RNA to give L-19 IVS RNA (Zaug, A. J., et al., Science 224, 574 (1984). The reaction was stopped by the addition of EDTA to 25 mM. The L-19 IVS RNA was purified by preparative gel electrophoresis and Sephadex G-50 chromatography. Labeled oligonucleotides were incubated with unlabeled L-19 IVS RNA at 42° C. in 20 mM MgCl$_2$, 50 mM tris, pH 7.5, for 0, 1, 2, 5, 10, 30, and 60 minutes. Reactions were stopped by the addition of EDTA to a final concentration of 25 mM. Products were analyzed by electrophoresis in a 20 percent polyacrylamide, 7M urea gel, autoradiograms of which are shown.

FIG. 6 Kinetics of conversion of pC$_5$ to larger and smaller oligonucleotdides with 1.6 uM L-19 IVS RNA. Products were separated by polyacrylamide gel electrophoresis. With the autoradiogram as a guide, the gel was cut into strips and the radioactivity in each RNA species was determined by liquid scintillation counting. The amount of reaction at each time was taken as the radioactivity in pC$_3$+pC$_4$+pC$_6$+pC$_7$+ ... divided by the total radioactivity in the lane. The initial velocity of product formation, V$_o$, was determined from a semilogarithmic plot of the fraction of reaction as a function of time. V$_o$ was then plotted as a function of substrate concentration; the line is a least-squares fit to the Michaelis-Menten equation. The resulting kinetic parameters are K$_m$=42 uM, V$_{max}$=2.8 uM min$^{-1}$, and k$_{cat}$=1.7 min$^{-1}$. The kinetic parameters for the first and second steps in the reaction have not yet been determined separately.

FIG. 7 Formation and resolution of the covalent enzyme-substrate intermediate. (A) To form the covalent L-19 IVS RNA-substrate intermediate, 8.5 nM C$_5$p* was treated with 0.16 uM L-19 IVS RNA under standard reaction conditions for 0 to 60 minutes. (B) p*C$_5$ (0.01 uM) was reacted with 0.16 uM L-19 IVS RNA. Cleavage occurred normally, but there was very little rejoining. (C) Labeled covalent intermediate was prepared as in (A) (60 minutes) and purified by electrophoresis in a 4 percent polyacrylamide, 8M urea gel. It was then incubated with 10 uM unlabeled C$_5$ under standard reaction conditions for 0 to 60 minutes. The product designated C$_6$ comigrated with labeled C$_6$ marker (not shown). (D) Isolated covalent intermediate as in (C) was incubated under site-specific hydrolysis conditions (20 mM MgCl$_2$, 50 mM CHES, pH 9.0) at 42° C. for 0 to 60 minutes. Positions of labeled mono- and dinucleotide markers are indicated. In the 10- and 30-minute lanes of (A) and the 10-, 30-, and 60-minute lanes of (C), band compression (reduced difference in electrophoretic mobility) is seen between C$_6$ and C$_7$ and to a lesser extent between C$_7$ and C$_8$. This is due to the absence of a 5' phosphate. Thus, the charge-to-mass ratio is increasing with chain length, whereas with 5'-phosphorylated oligonucleotides the charge-to-mass ratio is independent of chain length. When such products were phosphorylated by treatment with polynucleotide kinase and ATP, the distribution was converted to the normal spacing as in FIG. 1 [Zaug, A., et al. (unpublished data)].

Figure 8:
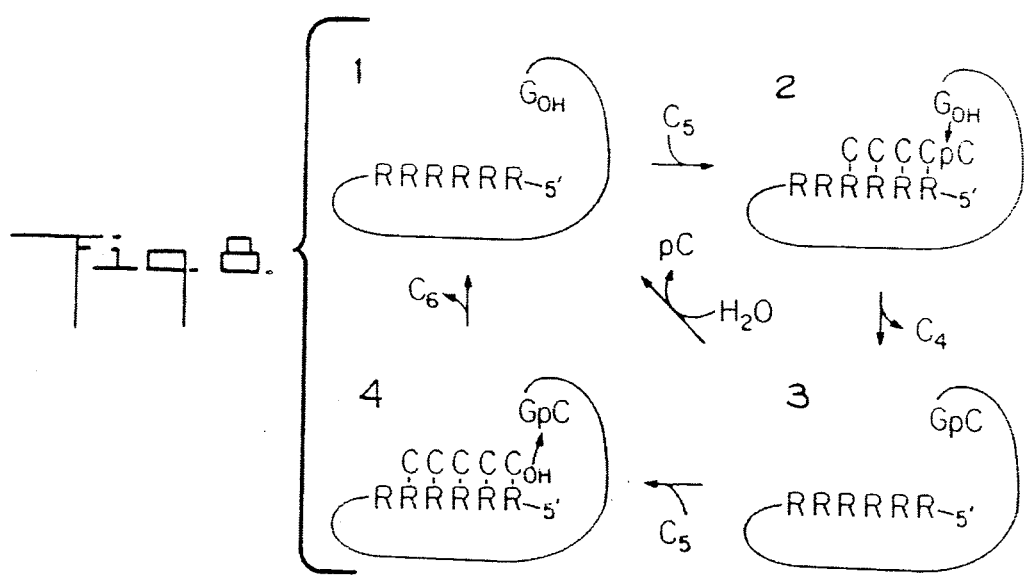
FIG. 8 is a model for enzymatic mechanism of L-19 IVS RNA acting as a ribonucleotidyl transferase.

FIG. 8 Model for the enzymatic mechanism of the L-19 IVS RNA. The RNA catalyzes cleavage and rejoining of oligo(C) by the pathway 1 - 2 - 3 - 4 - 1. The L-19 IVS RNA enzyme (1) is shown with the oligopyrimidine binding site (RRRRRR, six purines) near its 5' end and $G^{414}$ with a free 3'-hydroxyl group at its 3' end. The complex folded core structure of the molecule (Davies, R. W., et al., (1982) Nature (London) 300:719; Waring, R. B., et al. (1983) J. Mol. Biol. 167:595; Michel, F., et al. (1983) EMBO J. 2:33; Cech, T. R., et al. (1983) Proc. Nat'l. Acad. Sci. U.S.A. 80:3903; Inoue, T., et al. (1985) ibid 82:648) is simply represented by a curved line. The enzyme binds its substrate ($C_5$) by Watson-Crick base-pairing to form the noncovalent enzyme-substrate complex (2). Nucleophilic attack by $G^{414}$ leads to formation of the covalent intermediate (3). With the pentanucleotide $C_5$ as substrate, the covalent intermediate is usually loaded with a single nucleotide, as shown; with substrates of longer chain length, an oligonucleotide can be attached to the 3' end of $G^{414}$. If $C_5$ binds to the intermediate (3) in the manner shown in (4), transesterification can occur to give the new product $C_6$ and regenerate the enzyme (1). Note that all four reactions in this pathway are reversible. When acting as a ribonuclease, the L-19 IVS RNA follows the pathway 1 - 2 - 3 - 1. The covalent intermediate (3) undergoes hydrolysis, releasing the nucleotide or oligonucleotide attached to its 3' end (in this case pC) and regenerating the enzyme (1).

Figure 9A:
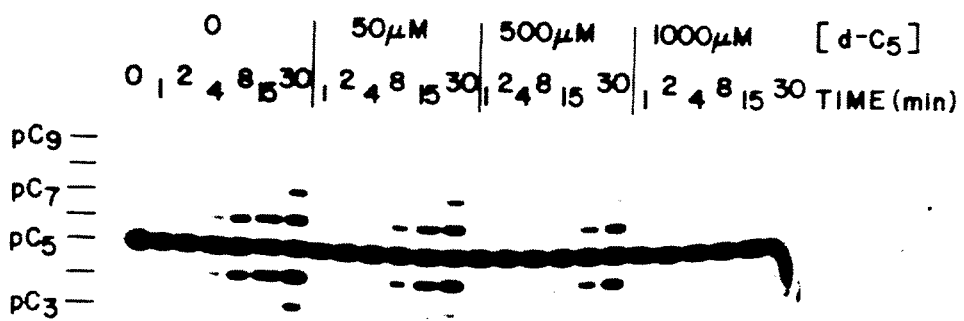
FIG. 9 shows the competitive inhibition of $pC_5$ reaction by $dC_5$.
Figure 9B:
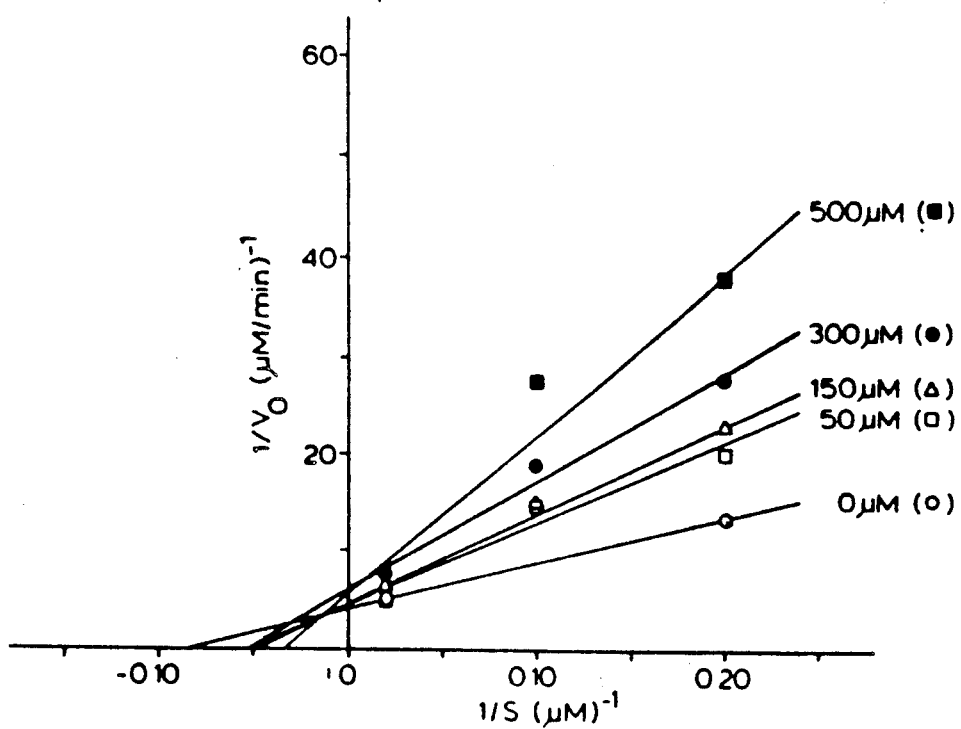
Figure 9C:
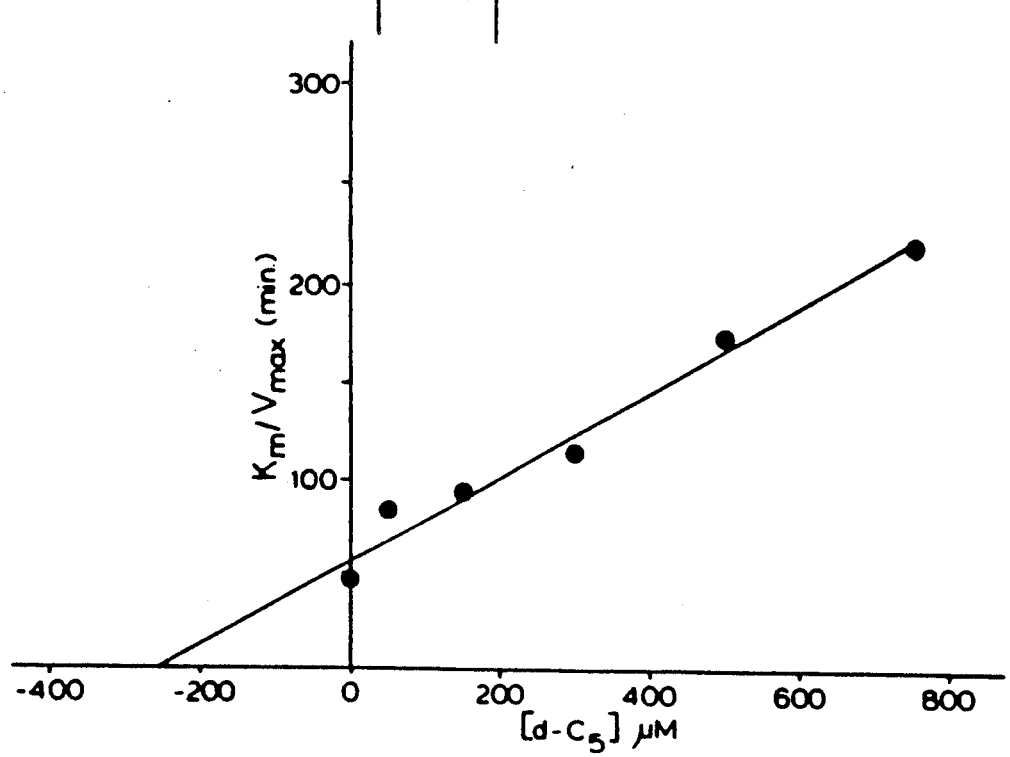

FIG. 9. Competitive inhibition of the $pC_5$ reaction by d-$C_5$. (A) 5 uM p*$C_5$, shown unreacted in lane O, was incubated with 0.16 uM L-19 IVS RNA under standard reaction conditions. Reactions were done in the absence of d-$C_5$ or in the presence of 50 uM, 500 uM, or 1000 uM d-$C_5$ as indicated. (B) Lineweaver-Burk plots of the rate of conversion of $pC_5$ to $pC_4 + pC_3$ in the presence of (o) 0 uM, (open square) 50 uM, (open triangle) 150 uM, (closed circle) 300 uM, or (closed square) 500 uM unlabeled d-$C_5$. The analysis was limited to the smaller products because their production is affected only by the first transesterification reaction (FIG. 8). Although d-$C_5$ is inactive in the first transesterification reaction, it has some activity as a substrate in the second transesterification reaction (Zaug, A., et al. unpublished data) and therefore could affect the production of chains of length greater than 5. (C $K_m/V_{max}$, determined from the slopes of the lines in (B), is plotted against the inhibitor concentration. The x-intercept gives the negative of $K_i$; $K_i = 260$ uM.

Figure 10:
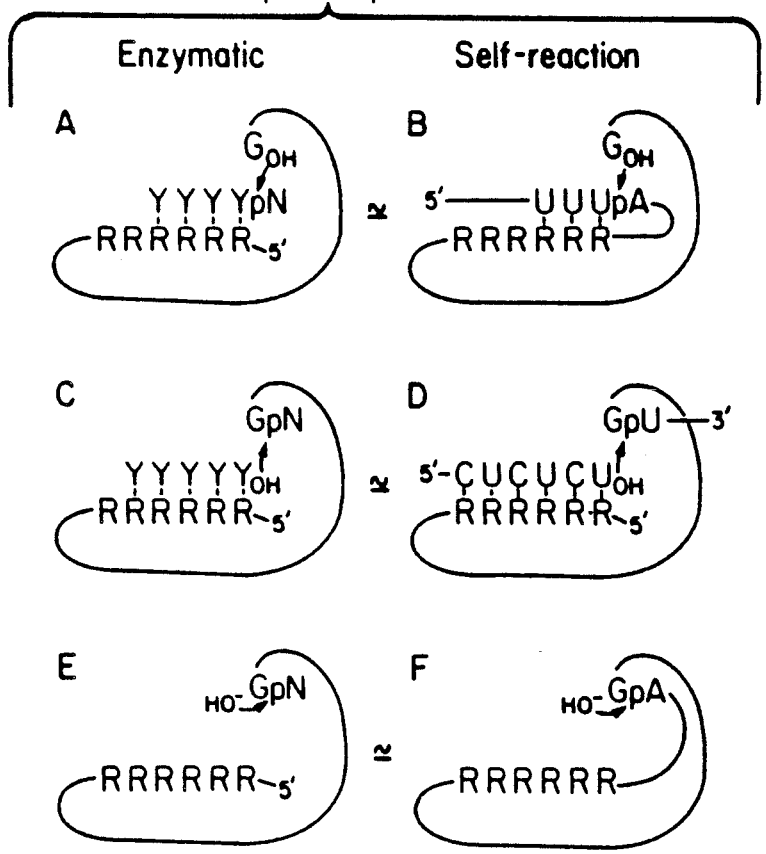
FIG. 10 shows the relation of reactions catalyzed by the L-19 IVS RNA to self-splicing and related IVS RNA-mediated reactions.

FIG. 10 Relation of reactions catalyzed by the L-19 IVS RNA to self-splicing and the related IVS RNA-mediated reactions. Formation of the covalent enzyme-substrate intermediate (A) is analogous to IVS RNA autocyclization (B). Resolution of the enzyme-substrate intermediate (C) is analogous to exon ligation (D) or the reversal of cyclization (Sullivan, F. X. and Cech, T. R. (1985) Cell 42:639). Hydrolysis of the enzyme-substrate intermediate (E) is analogous to site-specific hydrolysis of the circular IVS RNA (F) or the pre-rRNA (Inoue, T., et al. (1986) J. Mol. Biol. 189:143-165).

FIG. 11 The L-19 IVS RNA catalyzes the dephosphorylation of oligo(cytidylic acid) 3'-phosphate. (A) L-19 IVS RNA (0.16 uM) was incubated with p*$C_5$ (10 uM), p*$A_6$ (10 uM), $C_5$p*Cp(about 2 nM), and $A_6$p*Cp (about 3 nM) in 20 mM $MgCl_2$ and 50 mM Tris-HCl, pH 7.5, at 42° C. for the times indicated. Reaction products were separated by electrophoresis in a 20% polyacrylamide-7M urea sequencing gel, an autoradiogram of which is shown. (B) L-19 IVS RNA (0.2 uM) was incubated with $C_5$p* (about 2 nM) as above. The phosphoenzyme E-p* is the L-19 IVS RNA with a 3'-terminal phosphate monoester. Gel electrophoresis and autoradiography as in (A). Only a portion of the 5-min sample was loaded on the gel.

FIG. 12 Effect of pH on the phospho transfer and nucleotidyl transfer reactions. (A) Lane 1, untreated $C_5$p*Cp; lanes 2-11, $C_5$p*Cp (15 nM) incubated with excess L-19 IVS RNA (500 nM) in 20 mM $MgCl_2$ and 50 mM buffer (NaOAc for pH 4.0 and 5.0, Tris-HCl for pH 7.5, CHES for pH 9.0 and 10.0); lane 12, $C_5$p*Cp treated with calf intestinal phosphatase to provide a marker for $C_5$p*C—OH; lane 13, untreated p*$C_5$; lanes 14-23, p*$C_5$ (15 nM) incubated with excess L-19 IVS RNA (500 nM) as in lanes 2-11. Reactions proceeded at 42° C. for the indicated times, after which they were stopped by he addition of an equal volume of urea sample buffer containing 50 mM EDTA. (B) $C_5$p*Cp (about 2 nM) was incubated with L-19 IVS RNA (0.2 uM) at pH 5.0 for the times indicated. (C) Data similar to those shown in (B) except with 15 nM $C_5$p*Cp were quantitated by liquid scintillation counting of the sliced gel. Semilogarithmic plots, which were linear for the first three or four time points, were used to determine $t_{\frac{1}{2}}$. The observed first-order rate constant ($k_{obsd}$) was calculated as $(\ln 2)/t_{178}$. NaOAc buffer was used for pH 4.0 and 5.0, MES for pH 5.5 and 6.0, and Tris-HCl for pH 7 (estimate based on a single point that showed about 50% reaction).

Figure 13:
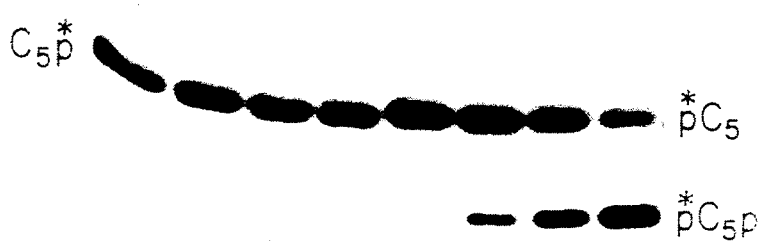
FIG. 13 shows that the phosphorylation of L-19 IVS RNA ribozyme is reversible.

FIG. 13. Phosphorylation of the enzyme is reversible. L-19 IVS RNA (0.2 uM) was phosphorylated by incubation with 2.5 uM unlabeled $C_5$p for min at 42° C. at pH 5.0. A trace amount of (A) $C_5$p* (1.2 nM) or (B)p*$C_5$(20 nM) was then added to the unlabeled E-p, and incubation was continued for the times shown.

FIG. 14. The L-19 IVS RNA acts catalytically as a phosphotransferase. (A) Decreasing concentrations of $C_5$p* were incubated for 30 min with 0.32 uM L-19 IVS RNA and 100 uM unlabeled UCU-OH. The specific radioactivity of $C_5$p* was adjusted by addition of unlabeled $C_5$p* to keep the amount of radioactivity constant among samples. The small amount of intermediate band seen in some reactions is presumed to be UCUCp formed by attack of UCU on an E-pCp covalent intermediate. (-lane) $C_5$p* prior to incubation. (B) $C_5$p* (2.5 uM) incubated with 0.16 uM L-19 IVS RNA and 200 uM unlabeled UCU-OH. (C) Quantitation of data shown in (B), including labeled E-p, which ran near the top of the gel. In all cases, incubation was in 20 mM $MgCl_2$ and 50 mM MES, pH 6.0, at 42° C.

FIG. 15. Single active site model for the activity of the L-19 IVS RNA on phosphate diester and phosphate monoester substrates. (A) Reversible nucleotidylation of the L-19 IVS RNA, proposed to be the key step in the poly(C) polymerase reaction (Zaug & Cech, (1986) Science (Wash. D.C. 231:470-475. (B) Reversible phosphorylation of the L-19 IVS RNA, which allows the enzyme to act as a phosphotransferase. In both cases, the oligo(C) substrate base pairs to the oligo(Pyrimidine) binding site (six R's) to form a noncovalent complex. The binding site is nucleotides 22-27 of the IVS RNA and has the sequence GGAGGG (M. D. Been and T. R. Cech, (1986) Cell 47:206-216). Nucleophilic attack by the 3'-hydroxyl of the active site guanosine, G414 leads to formation of E-pC (A) or E-p (B) and the release of $C_5$. The complex folded core structure of the IVS is depicted as a simple curved line.

FIG. 16 Plasmid pBGST7 contains a fragment with the IVS inserted into the multicloning site of a small pUC18 derivative which in turn contains a phage T7 promoter. The double line represents the plasmid DNA with the IVS. The relative positions of the promoters are indicated. The positions of the EcoRI and Hind III site are indicated by the arrowheads. The upper line represents the in vitro transcript made from purified plasmid DNA with phage T7 RNA polymerase. The numbers above it refer to the length, in nucleotides, of the exons and IVS. The lower line represents the in vivo transcript of the 5' end of lacZ'. The IVS (heavy line) contains stop codons in all three reading frames, so a functional alpha fragment can only be produced if the IVS is excised and the exons are joined by splicing in *E. coli*.

DESCRIPTION

The Tetrahymena rRNA intervening sequence (IVS) is a catalytic RNA molecule or ribozyme. It mediates RNA self-splicing, accomplishing its own excision from the large ribosomal RNA precursor, and subsequently converts itself to a circular form (Kruger, K., et al. (1982) Cell 31:147-157; Zaug, A. J., et al. (1983) Nature 301:578-583). In these reactions, the splice sites and cyclization sites can be viewed as intramolecular substrates for an activity that resides within the IVS RNA (Zaug, A. J., et al. (1984) Science 224:574-578). This is not a true enzymatic reaction however since the RNA is not regenerated in its original form at the end of the self-splicing reaction. The IVS RNA when in its linear form is referred to as L IVS RNA.

This view has been validated by studies of the L-19 IVS RNA, a linear form of the IVS which is missing the first 19 nucleotides. Because it lacks the cyclization sites, the L-19 IVS RNA cannot undergo intramolecular reactions (Zaug, A. J., et al. (1984) Science 224:574-578). It still retains activity, however, and can catalyze cleavage-ligation reactions on other RNA molecules (Zaug, A. J. and Cech, T. R. (1986) Science 231:470-475). When provided with oligo(cytidylic acid) as a substrate, the L-19 IVS RNA acts as an enzyme with nucleotidyltransferase [poly(C) polymerase] and phosphodiesterase (ribonuclease) activities (Zaug, A. J. and Cech, T. R. (1986) Science 231:470-475). With 3'-phosphorylated oligo(C) substrates, the same ribozyme acts as a phosphotransferase and an acid phosphatase (Zaug, A. J. and Cech, T. R. (1986) Biochemistry 25:4478-4482). A key mechanistic feature of all four of these reactions is the formation of a covalent enzyme-substrate intermediate in which a nucleotide or phosphate is esterified through the 3'-O of $G^{414}$, the 3' terminal guanosine of the IVS RNA. In addition, we describe herein a fifth enzymatic activity concerning the endoribonuclease activity of the L-19 IVS RNA on other RNA molecules.

Following self-splicing of the Tetrahymena rRNA precursor, the excised IVS RNA (Abbreviations: IVS, intervening sequence or intron: L-19 IVS RNA (read "L minus 19"), a 395-nt RNA missing the first 19 nt of the L IVS RNA (the direct product of pre-ribosomal RNA splicing); p*,$^{32}$P within an oligonucleotide, that is, $C_5$p*C is $CpCpCpCpC^{32}pC$ and p*$C_5$ is $^{32}pCpCpCpCpC$; d-$C_5$, deoxy$C_5$) undergoes a series of RNA-mediated cyclization and site-specific hydrolysis reactions. The final product, the L-19 IVS RNA is a linear molecule that does not have the first 19 nucleotides of the original excised IVS RNA (Zaug, A. J., et al., Science 224:574 (1984). We interpreted the lack of further reaction of the L-19 species as an indication that all potential reaction sites on the molecule that could reach its active site (that is, intramolecular substrates) had been consumed; and we argued that the activity was probably unperturbed (Zaug, A. J., et al., Science 224:574 (1984) (L IVS RNA is linear IVS RNA). We have now tested this by adding oligonucleotide substrates to the L-19 IVS RNA. We find that each IVS RNA molecule can catalyze the cleavage and rejoining of many oligonucleotides. Thus, the L-19 IVS RNA is a true enzyme. Although the enzyme can act on RNA molecules of large size and complex sequence, we have found that studies with simple oligoribonucleotides like p$C_5$ (pentacytidylic acid) have been most valuable in revealing the minimum substrate requirements and reaction mechanism of this enzyme.

Nucleotidyltransferase or RNA Polymerase Activity

When the shortened form of the self-splicing ribosomal RNA (rRNA) intervening sequence of *Tetrahymena thermophila* acts as a nucleotidyl transferase, it catalyzes the cleavage and rejoining of oligonucleotide substrates in a sequence-dependent manner with $K_m=42$ uM and $k_{cat}=2$ min$^{-1}$. The reaction mechanism resembles that of rRNA precursor self-splicing. With pentacytidylic acid as the substrate, successive cleavage and rejoining reactions lead to the synthesis of polycytidylic acid. When the active site is changed from the natural nucleotide sequence GGAGGG to the sequence GAAAAG, oligouridylic acid is polymerized to polyuridylic acid [Been and Cech, Cell 47:207 (1986)]. Thus, the RNA molecule can act as an RNA polymerase, differing from the protein enzyme in that it uses an internal rather than an external template. Thus various heteropolymers would be constructed by varient RNA enzyme forms. This predicts the formation for example of messenger RNA molecules for particular peptides or proteins. This messenger could be synthesized with or without introns. At about pH 9, the same RNA enzyme has activity as a sequence-specific ribonuclease.

With $C_5$ as substrate, the L-19 IVS RNA makes poly(C) with chain lengths of 30 nucleotides and longer, acting as an RNA polymerase or nucleotidyl transferase. Thus longer oligonucleotides (polynucleotides) can be formed from short oligonucleotide starting material The number of P—O bonds is unchanged in the process. In the synthesis of poly(C) on a poly(dG) template by RNA polymerase, one CTP is cleaved for each residue polymerized. Thus, the RNA polymerase reaction is also conservative with respect to the number of P—O bonds in the system. The L-19 IVS RNA can therefore be considered to be a poly(C) polymerase that uses $C_4$pC instead of pppC as a substrate. It incorporates pC units at the 3' end of the growing chain and releases $C_4$; the $C_4$ is analogous to the pyrophosphate released by RNA polymerase. Synthesis is directed by a template, but the template is internal to the RNA enzyme. It may be possible to physically separate the template portion from the catalytic portion of the RNA enzyme with retention of activity. If so, the RNA enzyme could conceivably act as a primordial RNA replicase, catalyzing both its own replication and that of other RNA molecules (T. R. Cech, (1986) Proc. Nat'l. Acad. Sci. USA 83:4360–4363.

The L-19 IVS RNA catalyzes the cleavage-ligation of pC$_5$ with $K_m=42$ uM, $k_{cat}=2$ min$^{-1}$, and $k_{cat}/K_m=1\times 10^3$ sec$^{-1}$ M$^{-1}$. The $K_m$ is typical of that of protein enzymes. The $k_{cat}$ and $k_{cat}/K_m$ are lower than those of many protein enzymes. However, $k_{cat}$ within the range of values for proteins that recognize specific nucleic acid sequences and catalyze chain cleavage or initiation of polymerization. For example, Eco RI restriction endonuclease cleaves its recognition sequence in various DNA substrates, including a specific 8-bp DNA fragment, with $k_{cat}=1$ min$^{-1}$ to 18 min$^{-1}$ (Greene, P. J., et al. (1975) J. Mol. Biol. 99:237; Modrich, et al. (1976) J. Biol. Chem 251:5866; Wells, R. D., et al. (1981) Enzymes 14:157; Brennan, M. B., et al. in preparation; and Terry, B., et al. in preparation). The $k_{cat}$ is also similar to that of the RNA enzyme ribonuclease P, which cleaves the precursor to tRNA with $k_{cat}=2$ min$^{-1}$ (Guerrier-Takada, C., et al. (1983) Cell 35:849; Marsh, T. L., et al. in Sequence Specificity in Transcription and Translation, R. Calendar and L. Gold Eds., UCLA Symposium on Molecular and Cellular Biology (Plenum, New York, in press).

Another way to gauge the catalytic effectiveness of the L-19 IVS RNA is to compare the rate of the catalyzed reaction to the basal chemical rate. A transesterification reaction between two free oligonucleotides has never been observed, and hence the uncatalyzed rate is unknown. On the other hand, the rate of hydrolysis of simple phosphate diesters has been studied (Kumamoto, J. et al. (1956) J. Am. Chem Soc. 78:4858; P. C. Haake et al. ibid (1961) 83:1102; Kirby, A. J., et al. (1970) J. Chem Soc. Ser. B., p. 1165; Bunton, C. A., et al. (1969) J. Org. Chem. 34:767)). The second-order rate constant for alkaline hydrolysis of the labile phosphodiester bond in the circular IVS RNA (Zaug, A. J., et al. (1985) Biochemistry 24:6211) is 12 orders of magnitude higher than that of dimethyl phosphate (Kumamoto, J., et al (1956) Supra) and ten orders of magnitude higher than that expected for a normal phosphodiester bond in RNA (The rate of nucleophilic attack by hydroxide ion on phosphate esters is sensitive to the p$K_a$ of the conjugate acid of the leaving group. A phosphate in RNA should be more reactive than dimethyl phosphate, because p$K_a=12.5$ for a nucleoside ribose and p$K_a=15.5$ for methanol [values at 25° C. from P.O.P. T'so, Basic Principles in Nucleic Acid Chemistry (Academic Press, New York, (1974), vol. I, pp. 462–463 and P. Ballinger and F. A. Long, J. Am. Chem. Soc. 82:795 (1960), respectively). On the basis of the kinetic data available for the alkaline hydrolysis of phosphate diesters (Kumamoto, J, et al. (1956) J. Am. Chem Soc. 78:4858; Haake, P. C. (1961) et al. ibid 83:1102; Kirby, A. J., et al (1970) J. Chem Soc. Ser. B., p. 1165; Bunton, C. A., et al. (1969) J. Org. Chem 34:767), the slope of a graph of the logarithm of the rate constant for hydrolysis as a function of p$K_a$ can be roughly estimated as 0.6. Thus, RNA is expected to be more reactive than dimethyl phosphate by a factor of $10^{0.6\,(15.5-12.5)} = 10^{1.8}$. The estimate for RNA pertains to direct attack by OH$^-$ on the phosphate, resulting in 3'-hydroxyl and 5'-phosphate termini. Cleavage of RNA by OH$^-$-catalyzed transphosphorylation, producing a 2',3'-cyclic phosphate, is a much more rapid (intramolecular) reaction but is not relevant to the reactions of the L-19 IVS RNA). On the basis of the data of FIG. 7D, the covalent enzyme-substrate complex undergoes hydrolysis at approximately the same rate as the equivalent bond in the circular IVS RNA. Thus, we estimate that the L-19 IVS RNA in its ribonuclease mode enhances the rate of hydrolysis of its substrate about $10^{10}$ times.

The RNA moiety of ribonuclease P, the enzyme responsible for cleaving transfer RNA (tRNA) precursors to generate the mature 5' end of the tRNA, is an example of an RNA enzyme molecule. (Guerrier-Takada, C., et al., (1983) Cell 35:849; Guerrier-Takada, C., et al. (1984) Science 223:285; Marsh, T. L., et al. in Sequence Specificity in Transcription and Translation, R. Calendar and L. Gold Eds., UCLA Symposium on Molecular and Cellular Biology (Plenum, New York, in press); Marsh, T. L., et al (1985) Science 229:79). However, this enzyme catalyzes only a specific tRNA reaction without general RNA activity. The specificity is such that a variety of single base changes in the t-RNA portion of the pre-tRNA substrate prevent the enzyme from cleaving the substrate.

Dephosphorylation Activity

We have also found that the same enzyme has activity toward phosphate monoesters. The 3'-phosphate of C$_5$p or C$_6$p is transferred to the 3'-terminal guanosine of the enzyme. The pH dependence of the reaction (optimum at pH 5) indicates that the enzyme has activity toward the dianion and much greater activity toward the monoanion form of the 3'-phosphate of the substrate. Phosphorylation of the enzyme is reversible by C$_5$—OH and other oligo(pyrimidines) such as UCU-OH. Thus, the RNA enzyme acts as a phosphotransferase, transferring the 3'-terminal phosphate of C$_5$p to UCU-OH with multiple turnover At pH 4 and 5, the phosphoenzyme undergoes slow hydrolysis to yield inorganic phosphate. Thus, the enzyme has acid phosphatase activity. These are the two aspects of its dephosphorylase activity. The RNA enzyme dephosphorylates oligonucleotide substrates with high sequence specificity, which distinguishes it from known protein enzymes.

The L-19 IVS RNA has transphosphorylation activity toward 3'-phosphorylated oligo(C) substrates. The properties of the transphosphorylation reaction indicate that it is taking place in the same active site as the poly(C) polymerase and ribonuclease reactions (FIG. 15). The properties include the specificity of the reactions for oligo(C) substrates, the production of oligo(C) products with 3'-hydroxyl termini, and the formation of similar covalent enzyme-substrate complexes. The presumptive intermediate is a phosphoenzyme, E-p, in the case of the phosphotransferase reaction and a nucleotidyl enzyme, E-pC or E-(pC)$_n$, in the case of the poly(C) polymerase and ribonuclease reactions (Zaug & Cech, (1986) Science (Wash., D.C. 231:470–475). In both cases the presumptive covalent intermediate involves a phosphate ester linkage through the 3'-0 of G414 of the L-19 IVS RNA (Zaug and Cech, unpublished results).

The transphosphorylation reaction is readily reversible. The phosphate can be transferred from the enzyme to an acceptor with a 3'-hydroxyl group, such as C$_5$ or UCU. With C$_5$p and UCU as cosubstrates, the L-19 IVS RNA can catalyze the reaction C$_5$p+UCU-OH —C$_5$—OH+UCUp. The proposed pathway is

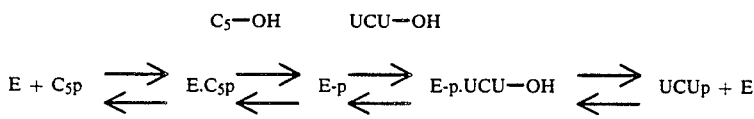

Thus, the L-19 IVS RNA has transphosphorylation activity resembling that of *Escherichia coli* alkaline phosphatase (Reid & Wilson, (1971) Enzymes (3rd Ed.) 4:373-415); Coleman & Gettins, (1983) Adv. Enzymol. Relat. Area Mol. Biol., 55:381), acid phosphatase, and a variety of other phosphotransferases that form covalent enzyme-substrate intermediates (Knowles, (1980) Ann. Rev. Biochem 49:877). In addition, the L-19 IVS RNA phosphoenzyme can transfer its phosphate to water at pH 4 and 5, indicating it has acid phosphatase activity.

As the pH is lowered from 7.5 to 5.0, the rate of the transphosphorylation reaction increases substantially. In this same pH range, the 3'-phosphate of $C_5p$ is converted to a monoanion [$pK_a$ approximately 6.0, based on the value for cytidine 3'-phosphate from Ts'o [(1974) Basic Principles in Nucleic Acid Chemistry vol. 1, pp. 462 Academic, N.Y.]. Protonation of a phosphate monoester makes it possible for it to react like a diester (Benkovic & Schray, (1973) Enzymes (3rd Ed.) 8:235). Thus, it seems reasonable that an enzyme known to react with diesters could use the same mechanism to react with monoester monoanions. The acidic pH requirement for hydrolysis of the phosphoenzyme can be similarly explained if the reaction occurs by attack of water on the phosphate monoester monoanion. The pH independence of transphosphorylation between pH 7.5 and pH 9.0 strongly suggests that the monoester dianion is also reactive, albeit at a rate less than 5% that of the monoester monoanion. The reactivity of the monoester dianion is surprising and perhaps indicates that the enzyme provides electrophilic assistance to the departure of the leaving group with a proton or metal ion.

At alkaline pH the phosphodiester bond following G414 is labile in the circular IVS RNA (Zaug et al., 1984 Science (Wash., D.C. 224:574), in the pre-rRNA (Inoue et al., 1986, J. Mol. Biol 189:143), and in E-pC (Zaug, A. J., and Cech, T., 1986, Science (Wash., D.C.) 231:470-475), whereas the phosphomonoester bond following $G^{414}$ is stable in E-p. Specific hydrolysis of the phosphodiester bonds involves attack of hydroxide ion (Zaug, A. J. et al., (1985) Biochemistry 24:6211). It is not surprising that attack of hydroxide ion on the phosphate monoester dianion of E-p might be prohibited due to electrostatic repulsion (Kirby & Younas, (1970) J. Chem. Soc. B, 1165).

At pH 5 the phosphoenzyme undergoes very slow hydrolysis but readily transfers its phospho group to $C_5$—OH. The rate of the hydrolysis reaction is 2-3 orders of magnitude slower than that of the phospho transfer reaction, even though $H_2O$ is present at 55M and the oligonucleotide at less than 1 uM. Thus, $C_5$—OH is a better acceptor than $H_2O$ by a factor exceeding $10^{10}$. [Such a large factor is not unusual for phosphotransferases; for example, Ray et al. (1976) Biochemistry 15:4006 report that phosphoglucomutase transfers a phosphate to the C-6 hydroxyl of glucose 1-phosphate at a rate $3 \times 10^{10}$ times greater than that of transfer to $H_2O$.] The difference in rate is much too large be explained by the greater nucleophilicity of the 3'-hydroxyl of $C_5$—OH than $H_2O$, which could perhaps account for a factor of 10 (Lohrmann & Orgel (1978) Tetrahedron 34:853; Kirby & Varvoglis, (1967) J. Am. Chem. Soc. 89:415-423). Most of the enzyme to utilize the binding reflects the ability of the enzyme to utilize the binding energy from its interaction with non-reacting portions of $C_5$—OH (Jencks, W. P., 1975, Adv. Enzymol. Relat. Areas Md. Biol. 43:219). For example, specific binding interactions could precisely position the 3'-hydroxyl of $C_5$—OH for displacement of the phosphate from the enzyme, but would not be available to facilitate the addition of water. Furthermore, the catalytic apparatus may not be fully assembled until the acceptor oligonucleotide is in place and water is absent (Koshland, (1963) Cold Spring Harbor Symp. Quant. Biol. 28:473; Knowles, (1980) Ann. Rev. Biochem. 49:877).

Figure 15A:
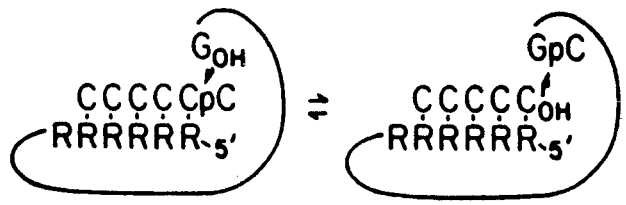
FIG. 15 shows the single active site model for the activity of L-19 IVS RNA on phosphate diester and phosphate monoester substrates
Figure 15B:
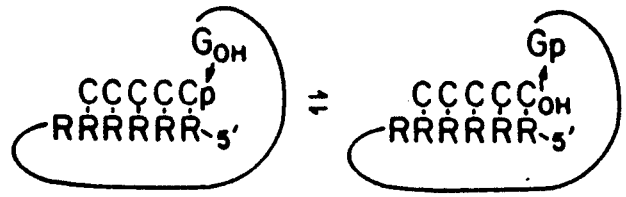

We are only beginning to understand how the L-19 IVS RNA catalyzes phospho transfer. The overall transfer reaction is undoubtedly facilitated by the formation of a covalent bond between the enzyme and the phosphate of the substrate. Such covalent catalysis is common in enzyme-catalyzed group transfer reactions (Jencks, (1969) Catalysis in Chemistry and Enzymology McGraw-Hill, New York; Walsh, (1979) Enzymatic Reaction Mechanisms W. H. Freeman, San Francisco). Binding sites within the IVS RNA for the oligo(pyrimidine) substrate (Zaug & Cech, (1986) Science (Wash., D.C. 231:470-475) and for the nucleophilic G residue at its own 3' end (N. K. Tanner and T. R. Cech, unpublished results) contribute to the catalysis of the transfer reactions. These binding interactions presumably place the 3'-hydroxyl group of G414 in an optimal orientation for nucleophilic attack on the terminal phosphate of $C_5p$ (FIG. 15B) or on an internal phosphate of $C_5$—OH (FIG. 15A). We suspect that catalysis might also involve a specific role for $Mg^{2+}$ [Steffens et al., (1973) J. Am. Chem. Soc. 95:936 and (1975) Biochemistry 14:2431; Anderson et al., (1977) J. Am. Chem. Soc. 99:2652; see also Zaug et al. (1985) Biochemistry 24:6211 and Guerrier-Takada et al. (1986) Biochemistry 25:1509] and general acid-base catalysis [see Cech and Bass (1986) Ann. Rev. Biochem. 55:599-629], but we have no direct evidence for such mechanisms. Applicants are not specifically bound by only those mechanisms discussed herein.

One unanswered question concerns the extremely low extent of nucleotidyl transfer with the $C_5p$ substrate at neutral pH. Since $C_5$—OH is readily attacked at the phosphate following the fourth C to produce E-pC, why is $C_5p$ not attacked at the equivalent phosphate to produce E-pCp? Perhaps the terminal phosphate of $C_5p$ is coordinated to Mg(II) or serves as a hydrogen bond acceptor, resulting in a preferred mode of binding different from that of $C_5$—OH.

Finding an enzyme that has both phosphodiesterase and phosphomonoesterase activity is unusual but not unprecedented. Exonuclease III (Richardson & Kornberg, (1964) J. Biol. Chem. 239:242-250), P1 nuclease, and mung bean nuclease (Shishido & Ando, 1982 in *Nucleases* (Linn, S. M. & Roberts, R. J. Eds) pp. 155-185, Cold Spring Harbor Laboratory, Cold Spring Harbor, N.Y.) all have 3'-phosphatase activity.

The L-19 IVS RNA is unique among known enzymes in its ability to remove 3'-phosphates from RNA with high substrate specificity. *E. coli* and mammalian alkaline phosphatases are nonspecific. These enzymes remove 5'-, 3'-, and 2'-phosphates from RNA with little regard for the base sequence of the molecule (Garen & Levinthal, (1960) Biochem. Biophys. Acta. 38:470; Harkness, (1968) Arch. Biochem. Biophys. 126:513). Polynucleotide kinase has 3'-phosphatase, 2'-phosphatase, and cyclic 2',3'-phosphatase activity (Cameron & Uhlenbeck, (1977) Biochemistry 16:5120; Weber, (1985) Ph.D. Thesis, University of Illinois). Substrates as diverse as $U_5p$, $A_6Cp$, and pCp are readily dephosphorylated, and where careful kinetic measurements have been made, the rates of dephosphorylation of different RNA substrates seldom vary by more than a factor of 2 (Weber, (1985) Supra). P1 nuclease and mung bean nuclease have limited preference for certain nucleoside 3'-monophosphates (Shishido & Ando, (1982) Supra). The L-19 IVS RNA, on the other hand, transfers the 3'-phosphate of RNA to a donor molecule with high substrate specificity; $C_5p$ and $C_6p$ are substrates, whereas pCp and $A_6$ pCp are not. This length and sequence specificity is explained by the requirement that the substance must bind to the enzyme by Watson-Crick base pairing to the guanosine-rich active site (FIG. 15). If this model is correct, it should be possible to alter the sequence specificity of the phosphotransferase by site-specific mutagenesis of the active site.

A series of sequence-specific 3'-phosphate dephosphorylating enzymes would provide a useful tool for RNA biochemistry and recombinant RNA manipulations. However, the RNA enzyme described here has cleavage-ligation activity as well as the dephosphorylation activity. Unless these activities can be separated, the usefulness of the enzyme as a reagent for dephosphorylation of RNA is limited.

Endoribonuclease or "RNA Restriction Endonuclease" Activity

We describe here a fifth enzymatic activity of the Tetrahymena ribozyme. It cleaves other RNA molecules at sequences that resemble the 5' splice site of the rRNA precursor. Cleavage is concomitant with addition of a free guanosine nucleotide to the 5' end of the downstream RNA fragment; thus, one product can be readily end-labeled during the reaction The reaction is analogous to the first step of pre-rRNA self-splicing (FIG. 1). Cleavage does not require nucleotide $G^{414}$ of the ribozyme; thus, unlike the first four activities, it does not involve formation of a covalent enzyme-substrate intermediate. Thus there exists as a result of the work of the invention sequence-specific endoribonucleases, protein-free i.e. able to act in the absence of protein, and composed of RNA, which are enzymatically active on other RNA molecules. These RNA ribozymes act on exogenous RNA. Thus the enzyme or ribozyme is composed of RNA and the substrate is RNA (or mixed RNA-DNA polymers).

Figure 3C:

The ribozyme has high specificity for cleavage after the nucleotide sequence CUCU; under stringent conditions it can discriminate against sites that have a 3-out-of-4 match to this recognition sequence. For example, in a solution containing 2.5M urea the ribozyme cleaves after CUCU while ignoring the related sequences CUGU and CGCU (FIG. 3c). The sequence specificity approaches that of the DNA restriction endonucleases (Nathans, D. and Smith, H. O. (1975) Annu. Rev. Biochem. 44:273-293). We further show that site-specific mutations in the active site of the IVS RNA, the so-called internal guide sequence (Davies, R. W., et al. (1982) Nature 300:719-724; Waring, R. B., et al. (1986) Nature 321:133-139) or 5' exon-binding site (Inoue, T., et al. (1985) Cell 43:431-437; Garriga, G., et al. (1986) Nature 322:86-89; Been, M. D. and Cech, T. R., (1986) Cell 47, 207-216), alter the sequence specificity of the ribozyme in a predictable manner. In its endoribonuclease mode, the L-19 IVS RNA recognizes four or more nucleotides in choosing a reaction site. Protein ribonucleases that are active on single-stranded RNA substrates have specificity only at the mononucleotide level (for example, ribonuclease $T_1$ cleaves after guanosine). Thus the L-19 has more base-sequence specificity for single-stranded RNA than any known protein ribonuclease, and may approach the specificity of some of the DNA restriction endonucleases. An attractive feature of this new RNA enribonuclease is that its substrate specificity can be completely and predictably changed by altering the sequence of the internal binding site.

The endoribonuclease reaction is analogous to the first step of pre-rRNA self-splicing (FIG. 1). Both the enzymatic and the self-splicing reactions make use of the same two binding sites, an oligopyrimidine-binding site and a guanosine-binding site, to achieve specificity and to contribute to catalysis. The oligopyrimidine-binding site is also known as the 5' guide sequence (Waring, R. B., et al. (1986) Nature 321:133-139) or the 5' exon-binding site (Inoue, T., et al. (1985) Cell 43:431, Garriga, G., et al. (1986) Nature 322:86-89, Been, M. D. and Cech, T. R., Cell (1986) 47, 207-216). Its role in self-splicing has been conclusively demonstrated by the analysis of single-base mutations and second-site suppressor mutations (Waring, R. B., et al. (1986) Supra; Been, M. D. and Cech, T. R., (1986) Supra; Perea, J. and Jacq, C., (1985) EMBO, J. 4:3281). The role of these same nucleotides in the endoribonuclease reaction is demonstrated by the change in substrate specificity of the mutant enzymes (FIG. 3), the altered specificity being predictable by the rules of Watson-Crick. base pairing. The guanosine-binding site involved in self-splicing has not been localized to a particular set of nucleotides, but its general features have been described (Bass, B. L. and Cech, T. R., (1984) Nature 308:820; (1986) Biochemistry 25:4473). The endoribonuclease activity appears to make use of the same guanosine-binding site by the following criteria: in both cases guanosine is as active as GTP, whereas UTP, CTP, ATP and dGTP have little if any activity. In addition, the $K_m$ of 44 uM for GTP shown is in reasonable agreement to the value of $32\pm 8$ uM determined for self-splicing under somewhat different reaction conditions (Bass, B. L. and Cech, T. R., Biochemistry (1986) Supra).

The endoribonuclease activity of the L-19 IVS RNA does not require its 3'-terminal guanosine ($G^{414}$). In this respect it differs from the nucleotidyl transfer, phospho transfer and hydrolytic activities of the same enzyme. In those reactions $G^{414}$ participates in a covalent enzyme-substrate complex that appears to be an obligatory reaction intermediate (Zaug, A. J. and Cech, T. R. (1986) Science 231:470-475; Zaug, A. J. and Cech, T. R. (1986) Biochemistry 25:4478). Thus, the L-19 IVS RNA is not restricted to reaction mechanisms involving formation of a covalent enzyme-substrate intermediate. It an also catalyze bisubstrate reactions by a single-displacement mechanism. Ribonuclease P, an RNA enzyme that catalyzes cleavage by hydrolysis rather than by transesterification, also appears to act without formation of a covalent intermediate (Marsh, T. L., et al. (1985) Science 229:79-81; Guerrier-Takeda, C., et al. (1986) Biochemistry 25:1509).

The L-19 IVS RNA endoribonuclease activity reported here appears to require single-stranded RNA substrates. Based on work recently reported by Szostak ((1986) Nature 322:83-86), it seems possible that a smaller version of the Tetrahymena IVS RNA missing its 5' exon-binding site may have an endoribonuclease activity that requires a base-paired substrate. The substrate tested by Szostak ((1986) Nature Supra) was an RNA fragment containing the end of the 5' exon paired with the 5' exon-binding site. However, this RNA "substrate" also included a substantial portion of the IVS RNA, so it remains to be established whether the ribozyme has endoribonuclease activity with double-stranded RNA substrates in general.

Potential usefulness of sequence-specific RNA endoribonucleases. Sequence-specific endoribonucleases might have many of the same applications for the study of RNA that DNA restriction endonucleases have for the study of DNA (Nathans, D. and Smith, H. O., (1975) Ann. Rev. Biochem. 44:273). For example, the pattern of restriction fragments could be used to establish sequence relationships between two related RNAs, and large RNAs could be specifically cleaved to fragments of a size more useful for study. The 4-nucleotide specificity of the ribozyme is ideal for cleavage of RNAs of unknown sequence; an RNA of random sequence would have an average of 1 cleavage site every 256 bases. In addition, the automatic end-labelling of one fragment during ribozyme cleavage is a practical advantage.

Development of the ribozymes as useful tools for molecular biology has begun. The efficiency of cleavage of large RNA substrates needs to be increased so that complete digests rather than partial digests can be obtained. The effects of denaturants such as urea and formamide must be further explored; they appear to increase the sequence specificity of cleavage, and at the same time they should melt structure in the substrate to maximize the availability of target sequences. Finally, mutagenesis of the active site of the ribozyme by those skilled in the art can be accomplished to ascertain all possible permutations of the 256 possible tetranucleotide cleavage enzymes.

RNA sequence recognition. Protein ribonucleases can cleave RNA substrates with high specificity by recognizing a combination of RNA structure and sequence, with the emphasis on structure (e.g., RNase III (Robertson, H. D. (1982) Cell 30:669) and RNase M5 (Stahl, D. A., et al. (1980) Proc. Natl. Acad. Sci. USA 77:5644). Known proteins that cleave single-stranded RNA substrates, on the other hand, have specificity only at the mononucleotide or dinucleotide level (e.g., RNase T$_1$ cleaves after guanosines [Egami, F., et al. (1980) Molec Biol. Biochem. Biophys. 32:250-277]. Thus, the L-19 IVS RNA has considerably more base-sequence specificity for cleaving single-stranded RNA than any known protein ribonuclease.

Variant Ribozymes (or other versions of the ribozyme that retain activity)

Earlier work on sequence requirements for self-splicing (Price, J. V., et al. (1985) Nucleic Acid. Res. 13:1871) show that sequence requirements can be examined as shown therein by insertions and deletions to obtain other self-splicing IVS RNA's. In like manner, we could alter the L-19 IVS RNA to obtain an array of RNA sequence-specific endoribonuclease molecules. Thus three regions were found by Price et al. to be necessary for IVS self-splicing. Similar experiments would reveal necessary portions of L-19 IVS RNA for endoribonuclease activity. Burke, J. M., et al. (1986) Cell 45:167-176 show the role of conserved elements for the IVS self-splicing sequence; that work shows a further use of mutagenesis experiments to alter the highly conserved sequences to alter activity thereof. Just so, in like manner, the activity of the L-19 IVS RNA can be altered with accompanying alteration in activity to effect an array of endoribonucleases.

Cech, T. R., et al. have recently found a yet smaller piece of the L-19 IVS RNA which contains full enzymatic activity and comprises nucleotides 19-331 of the RNA. It is also found that the 21-331 piece is fully active. Plasmids have been constructed to produce the L-19 and L-21 IVS RNA strands directly. Here the promoter is moved to the 19 position or 21 position and the DNA coding for the restriction site is at the 331 position instead of the 414 site.

Been, M. D and Cech, T. R. ((1986) Cell 47:207) show alteration in the specificity of the polymerase activity to effect polymerase activity with respect to oligo U using site-specific mutagenesis. Thus those skilled in the art can readily use the above to obtain other active L-19 IVS RNA enzymes.

Waring, R. B. and Davies, (1984) Gene 28:277 show a class of IVS RNA molecules with similar structure. This work is similar to that of Cech, T. R., et al. (1983) Proc. Natl. Acad. Sci. USA 80:3903 showing a class of fungal mitochondrial RNA IVS molecules. Some of these other IVS molecules have been found to be self-splicing. (Cech, T. R., et al. (1981) Cell 27:487; Kruger, K., et al. (1982) ibid. 31:147; Garriga, G., et al. (1984) ibid 39:631; Van der Horst, G., et al. (1985) ibid 40:759; Chu, F. K., et al. (1985) J. Biol. Chem. 260:10680; Peebles, C. L., et al. Cell in press; Van der Veen, R., et al., ibid. in press) Thus a series, or many series or class, or family of endoribonucleases from the same or other natural sources can be based on the work of the invention. Those skilled in the art will be able to search out other RNA enzymes from various natural sources.

The following RNA sequence elements can be considered to provide the minimum active site for ribozyme activity, based on (Cech, et al., PNAS (1983) and Waring & Davies Supra). Elements A and B interact with each other, as do 9L and 2. In many positions of the sequence, more than 1 base is allowed; the observed substitutions are shown by printing a letter directly below the base for which it can substitute. For example, at position 1 in sequence element A, the nucleotides A and U are observed, A being more common.

| A (also called P) | B (also called Q) |
|---|---|
| 1 2 3 4 5 6 7 8 9 10 | optional |
| 5'-A UGCUGGAAA | 5'-AAUCA(C)GCAGG |
| U     GAAAG U | U CUU  C    C |
|     G | |

| 9L (also called R) | 2 (also called S) |
|---|---|
| N = any base | |
| 5'-UCAGAG̅A̅C̅U̅A̅NA | AAGAUAU̅A̅G̅U̅C̅ |
| U AC | U G |
| C | |

-continued these pair namely GACUA on left and UAGUC on right
as underlined;
compensatory base changes
are allowed - see Burke, et al.
(1986) Supra The linear sequence of non-template DNA coding for L IVS RNA is shown below. Coding for the L-19 IVS RNA "ribozyme" begins at the site indicated by the arrow and extends to the end ($G^{414}$). Of course, in RNA the T's are U's.

```
                    L-19                                              53
                     ─▶
GAAATAGLAATATTTACCT│TTGGAGGGAAAAGTTATCAGGCATGCACCTGGTA
                   │ │ \ \ \
                   22 23 24 25

105
GCTAGTCTTTAAACCAATAGATTGCATCGGTTTAAAAGGCAAGACCGTCAAA

157
TTGCGGGAAAGGGGTCAACAGCCGTTCAGTACCAAGTCTCAGGGGAAACTTT

209
GAGATGGCCTTGCAAAGGGTATGGTAATAAGCTGACGGACATGGTCCTAACC

261
ACGCAGCCAAGTCCTAAGTCAACAGATCTTCTGTTGATATGGATGCAGTTCA

310
CAGACTAAATGTCGGTCGGGGAAGA  T  GTATTCTTCTCATAAGATATAGT

362
CGGACCTCTCCTTAATGGGAGCTAGCGGATGAAGTGATGCAACACTGGAGCC

414
GCTGGGAACTAATTTGTATGCGAAAGTATATTGATTAGTTTTGGAGTACTCG
```

In the discussion of L-19 IVS RNA, the region of the active site sequence discussed with respect to activity and variants is:

U U G G A G G G
20 21 22 23 24 25 26 27

The first ribonucleotide for the L-19 IVS RNA at the 5'OH end is the equivalent of the nucleotide 20 of the intact L IVS RNA. As regards positions 23, 24, 25 etc., there are positions 23, 24, 25 of the L IVS RNA (as if the first 19 positions were present).

Since $dC_5$ binds to the L-19 IVS RNA (see above), it is likely that the endoribonucleases will work on mixed polymers of RNA and DNA. For example, L-19 IVS RNA will bind the DNA portion while the RNA enzyme works on the RNA piece of the mixed polymer. Alteration of the binding site to bind the other nucleotides will result in an array of mixed polymer activity in a series of such endoribonucleases.

Abbreviations: IVS, intervening sequence; L-19 IVS RNA (read "L minus 19"), a 395-nucleotide linear RNA missing the first 19 nucleotides of the IVS; CHES,2-(cyclohexylamino)ethanesulfonic acid; EDTA, ethylenediaminetetraacetic acid; MES, 2-(N-Morpholino)-ethanesulfonic acid; Tris, tris(hydroxymethyl)aminomethane; p*, $^{32}P$ within an oligonucleotide (for example, $C_5p^*$ is $CpCpCpCpC[^{32}P]$-pCp).

Enzyme Preparation. L-19 IVS RNA can be synthesized and purified as described by Zaug and Cech (1986) Science (Wash., D.C.) 231:470–475 (see FIG. 5 for detailed description). In brief, RNA was transcribed from pSPTT1A3 with bacteriophage SP6 RNA polymerase in vitro. (Alternatively RNA can be transcribed from pT7-TT1A3 or from any of the plasmids in the pBG series with bacteriophage T7 RNA polymerase in vitro). Transcripts were further incubated to promote self-splicing and cyclization of the IVS RNA. The RNA was subsequently incubated in $MgCl_2$ at pH 9.0 (site-specific hydrolysis conditions) to convert circular IVS RNA to L-19 IVS RNA. The L-19 IVS RNA was purified by polyacrylamide gel electrophoresis and Sephadex G-50 chromatography. Enzyme concentration was determined by spectrophotometry assuming a molar extinction coefficient at 260 nm of $3.26 \times 10^6$ $M^{-1} cm^{-1}$.

Active plasmids in use are as follows:
pSPTT1A3, pT7-TT1A3, pBGST7, pBG/-2G:23C, pBG/23C, pBG/-3G:24C, pBG/24C, pBG/-4G:25C, pBG/25C, and pBG/23A4 and pT7L-21. The PBG plasmid series is described in Been, M. and Cech, T. R. (1986) Cell 407:207. For example, the pBG/3G:24C and the pBG/24C5plasmids produce the L-19 IVS RNA 24C variant which cleaves RNA after the CGCU 4 base sequence. These plasmids are on deposit and available at the Department of Chemistry and Biochemistry, University of Colorado, Boulder, Col. 80309-0215. Examples of these including pBG ST7 (ATCC 40288), pT7-TT1A3 (ATCC 40290) and pBG/-3G:24C (ATCC 40289) have been deposited with the American Type Culture Collection (ATCC) 12301 Parklawn Drive, Rockville Md. 20301 on Nov. 25, 1986. The plasmid pT7L-21 makes the L-21 IVS RNA wherein the first 21 bases are deleted. This plasmid (ATCC 40291) was also placed on deposit at the ATCC on Dec. 2, 1986.

Preparation of Substrates. $C_5p^*Cp$ and $A_6p^*Cp$ were prepared from $C_5$—OH and $A_6$—OH, respectively, with $T_4$ RNA ligase (New England Nuclear), $p^*Cp$, and ATP. Products were purified by 20% polyacrylamide-7M urea gel electrophoresis and Sephadex G-25 chromatography. $C_5p^*$ was prepared from $C_5p^*Cp$ by treatment with calf intestinal phosphatase and beta-elimination (Winter & Brownlee, 1978 Nucleic Acid. Res. 3129). Unlabeled $C_5p$ was prepared in a similar manner with unlabeled pCp as donor in the ligase reaction. Concentration was determined by spectrophotometry using a molar extinction coefficient at 270 nm of $30 \times 10^3 M^{-1} cm^{-1}$.

Preparation of E-p*. Unlabeled L-19 IVS RNA (16 pmol) was incubated with 5.2 pmol of C$_5$p* in 50 mM NaOAc, pH 5.0, and 20 mM MgCl$_2$ at 42° C. for 10 min. The reaction was stopped by the addition of EDTA to 40 mM. The E-p* was purified from unreacted C$_5$p* by column chromatography on Sephadex G-100-120, which was equilibrated in 0.01M Tris-HCl, pH 7.5, 0.25M NaCl, and 0.001M EDTA. The fractions that contained E-p* complex were pooled and precipitated with 3 volumes of ethanol. The dried precipitate was then dissolved in H$_2$O.

Standard Nucleotidyl Transferase Reaction Conditions

The oligoribonucleotide substrate (for example 10-100 uM pC$_5$) is incubated with ribozyme (for example 0.1-2.0 uM L-19 IVS RNA) at 42° C. in 20 mM Mgcl$_2$ and 50 mM Tris, pH 7.5 for 1 hour.

Standard Transphosphorylase Conditions

The 3'-phosphorylated RNA substrate (for example 2.5 uM C$_5$p) is incubated with ribozyme (for example 0.1 uM L-19 IVS RNA) and an acceptor oligonucleotide (for example, 200 uM UpCpU) at 42° C. in 20 mM MgCl$_2$ and 50 mM MES, pH 6.0 for 3 hours.

Standard Acid Phosphotase Conditions

The 3' phosphorylated RNA substrate (for example 2.5 uM C$_5$p) incubated in equimolar concentration of ribozyme (for example 2.5 uM L-19 IVS RNA) at 42° C. in 20 mM MgCl$_2$ and 50 mm NaC$_2$H$_3$O$_2$ (Na acetate), pH 5.0 for 24 hours.

Standard Endoribonuclease Reactions

Substrate RNA is pretreated with glyoxal according to the procedure of Carmichael and McMaster (1980) Meth in Enzymol. 65:380-391 and then ethanol precipitated and the precipitate pelleted by centrifugation in an eppendorf centrifuge. The pellet is dried and the RNA re-suspended in water. The glyoxylated substrate RNA (0.2 uM) is incubated with ribozyme (for example L-19 IVS-beta RNA, 0.2 uM) at 50° C. in 10 mM MgCl , 10 mM NaCl, 50 mM Tris-HCl pH 7.5, 0.5 mM GTP, 2.5M Urea for 1 hour.

Stopping Reactions and Analyzing Products

In all cases reactions are stopped by the addition of EDTA to a final concentration of 25 mM. Products can be analyzed by electrophoresis in a 20% polyacrylamide, 7.0M Urea gel (standard sequencing gel). If $^{32}$P-labelled RNA substrates are used, products can be localized by autoradiography.

The following Examples and the standard conditions above serve to illustrate, but not to limit the invention.

EXAMPLE I

Sequence-specific cleavage of large RNAs:

The L-19 IVS RNA enzyme was prepared by incubation of pre-rRNA under conditions that promote self-splicing, cyclization, and site-specific hydrolysis, (Zaug, A. J., et al. (1984) Science 224:574; Zaug, A. J., et al. (1986) Science 231:470). The 3'-terminal guanosine (G$^{414}$) was then removed from the L-19 IVS RNA by periodate oxidation followed by beta-elimination (Winter, G., et al. (1978) Nucleic Acids Res. 5:3129-3139). As expected, the resulting ribozyme (L-19 IVS-beta) has greatly reduced activity as a nucleotidyl-transferase, assayed using [$^{32}$P]-p(C)$_5$ as a substrate. When GTP was added, however, the ribozyme was able to cleave p(C)$_5$ as well as large RNA molecules. For example, the 504 nt pAK105 transcript (Mount, S. M., et al. (1983) Cell 33:509-518), a fragment of mouse beta-globin pre-mRNA containing the first intron, was cleaved to give major fragments of 148, 360 and 464 nt, as well as some minor fragments (FIG. 2a). As shown below, the 360 and 148 nt fragments can be explained as the 5' and 3' products of cleavage at position 360. The 464 nt fragment is the 3' product of cleavage at position 44, the 5' 44 nt fragment being to small to be observed. The absence of a major amount of a 316 nt RNA, the expected product of cleavage at both position 44 and 360, is indicative of partial digestion with few molecules cleaved more than once.

Cleavage required magnesium ion (optimum at 10-20 mM MgCl$_2$) and was essentially independent of monovalent cation the range 0-200 mM NaCl. The pH optimum was in the range of 7.5-8.0, and the temperature optimum was approximately 50° C. Although the beta-eliminated L-19 IVS RNA was competent to catalyze the cleavage reaction, removal of G$^{414}$ from the ribozyme was not required for cleavage activity. The enzyme worked at the same rate whether or not G$^{414}$ had been removed. We explain the activity of the intact L-19 IVS RNA by the postulate that, at saturating concentrations of GTP, the attack by GTP on the substrate competes very effectively with attack by G$^{414}$.

We note the IVS RNA and L-19 IVS RNA are protein-free. The L-19 IVS RNA is therefore a protein-free RNA enzyme (or ribozyme). L-19 IVS RNA and the like also function as enzymes in the absence of proteins. This applies to exogenous as well as endogenous protein. This is evidenced by retention of activity when subjected to protease activity, boiling or sodium dodecyl sulfate. Any RNA polymerase protein from the transcription system used to produce IVS RNA is removed by phenol extraction. The ability to make the IVS RNA in a totally defined system in vitro and remove the RNA polymerase by phenol extraction is further evidence of the protein-free nature of the reaction.

EXAMPLE II

Labelled cleavage products:

When [alpha-$^{32}$P]GTP was included in the reaction of pAK105 RNA as in Example I above, the 148 and 464 nt cleavage products were labeled (FIG. 2b). Direct sequencing of these labeled RNA fragments (e.g., FIG. 2c) showed that cleavage and GTP-addition occur at nucleotides 44 and 360 in the sequence, such that the downstream cleavage products are 5'-GTP labeled. The bonds formed by GTP addition are sensitive to RNase T$_1$, confirming that the GTP was covalently added through its 3'-0 by a normal 3'-5' phosphodiester bond. Reaction of the 841 nt pT7-1 (Xmn 1) RNA (essentially pBR322 sequences) produced 4 major labeled fragments. These were sequenced in the same manner. pT7-1 RNA with an additional 122 nt at its 3' end, produced by transcription of pT7-1 DNA that had been cleaved at the Sca I site, showed the expected increase in molecular weight of the labeled products. In all of the reactions, including those in which substrate RNA was omitted, the L-19 IVS RNA became labeled, perhaps by the guanosine-exchange reaction proposed elsewhere (Zaug, A. J., et al. (1985) Science 229:1060-1064; Price, J. V., et al. (1987) J. Mol. Biol. in press). The sites of self-labeling were heterogeneous.

EXAMPLE III

Specificity Assessment:

The sequence near the 5' end of each end-labeled product (See Example II above) was compared to the known sequence of the RNA to identify the nucleotides preceding the site of cleavage. The results are summarized in Table 1. Both the major and the minor cleavage sites are preceded by four pyrimidines, the consensus sequence being CUCU. This is exactly the tetranucleotide sequence expected to be an optimal target for the ribozyme. The importance of nucleotides at positions −5 and −6 relative to the cleavage site is not yet clear, although the absence of G residues may be significant. There is no apparent sequence preference downstream from the cleavage site, with all four nucleotides represented at position +1.

In assessing specificity, it is also necessary to consider which potential sites in the RNA were not cleaved by the ribozyme. For the pAK105 RNA, there was only one CUCU site at which cleavage was not observed. (Cleavage at this site would have produced a labeled 378 nt RNA.) On the other hand, a great many sites that match CUCU in 3 out of 4 positions were not cleaved. These include 17 CUMU sequences (where M≠C) and 7 CNCU sequences (where N≠U). In pT7-1 RNA, cleavage was observed at both the CUCU sequences in the RNA, but at only one of the 15 UUUU sequences present. Thus, the ribozyme has a strong preference for cleavage after the tetranucleotide CUCU.

EXAMPLE IV

Cleavage within regions of base-paired RNA secondary structure:

M1 RNA, the RNA subunit of *E. coli* RNase P (Reed, R. E., et al. (1982) Cell 30:627–636), was not cleaved by L-19 IVS RNA-beta under standard reaction conditions (FIG. 2b). M1 RNA contains the sequence UCCUCU, which should be an excellent targent site. However, this sequence is involved in a stable hairpin stem (Guerrier-Takada, C., et al. (1984) Biochemistry 23:6327–6334; Pace, N. R., et al. (1985) Orig. of Life 16:97–116), which presumably makes it unavailable as a substrate. We have found that denaturation of M1 RNA with glyoxal allowed efficient cleavage of this site by L-19 IVS RNA, in support of the interpretation that RNA secondary structure can inhibit cleavage. The glyoxal procedure used for denaturation is according to Carmichael, G. G., et al. (1980) Meth. in Enzymol 65:380–391.

EXAMPLE V

Active-site mutations alter substrate specificity:

The substrate specificity was next studied in a defined system where we could be certain that secondary structure in the substrate RNA was not affecting the cleavage reaction. Oligoribonucleotide substrates were synthesized by the phage T7 RNA polymerase transcription method developed by Uhlenbeck and co-workers (Lowary, P., et al. (1986) NATO ASI Series, vol. 110, 69–76) (FIG. 3a). One substrate contained a perfect match to the tetranucleotide consensus sequence. Two other substrates had single-base changes giving a 3-out-of-4 match to the consensus.

These substrates were tested with the wild-type L-19 IVS RNA and with two altered ribozymes (Been, M. D. and Cech, T. R., (1986) Cell 47,207–216). The two variants have single-base changes in the 5' exon-binding site that alter the sequence specificity of the first step in pre-rRNA self-splicing (Been, M. D., et al. Supra) The 23C variant (G converted to C at position 23 of the L-19 IVS RNA) is expected to recognize CUGU substrates, and the 24C (A converted to C at position 24) variant should recognize CGCU (FIG. 3b). In the course of these studies we found that the inclusion of 2.5M urea or 15% formamide in the reactions greatly increased the specificity, allowing each ribozyme to differentiate substrates with a single base change in the recognition sequence. Our operating model is that these denaturants destabilized the base-pairing between the substrate and the active site nucleotides of the ribozyme, thereby discriminating against mismatched complexes. The results of treatment of the 3 substrates with each of the 3 ribozymes in the presence of 2.5M urea are shown in FIG. 3c. Each substrate is cleaved exclusively by the ribozyme that is capable of making a perfectly base-paired enzyme-substrate complex (FIG. 3b). Thus it is contemplated the active site can be manipulated to recognize any base sequence so far that is XYZU, where X, Y and Z can be any of the four bases A,U,C,G and the nucleotides in the four base sequence can be the same or different.

When variant ribozymes were incubated with the 504 nt pAK105 RNA, each ribozyme gave a different pattern of cleavage products. One major cleavage site has been mapped for three variant ribozymes, including a 25C variant (G converted to C at position 25). The sites cleaved by the 23C, 24C and 25C ribozymes are preceded by CCCUGU, UCUGCU, and CUGUCU, respectively; the underlining indicates the base that would form a G.C base pair with the mutated nucleotide in the variant ribozyme. Each of these sequences can form 6 continuous base-pairs with the active site nucleotides of the variant ribozyme. While more cleavage sites must be sequenced before specificity can be properly assessed, these initial results are promising.

EXAMPLE VI

Figure 4A:
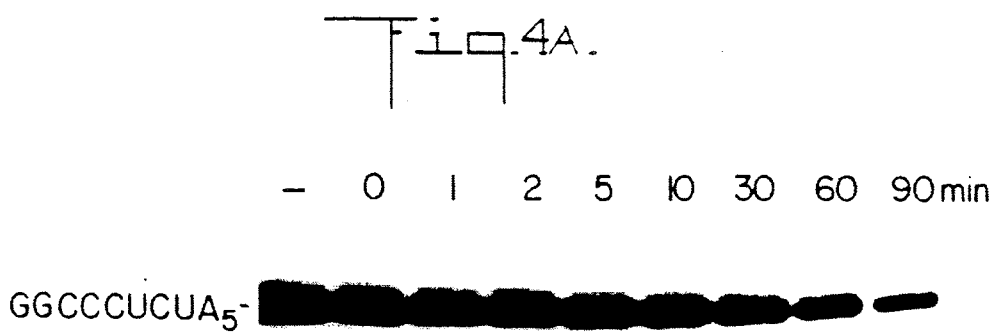
FIG. 4 shows the time course of oligonucleotide cleavage.
Figure 4B:
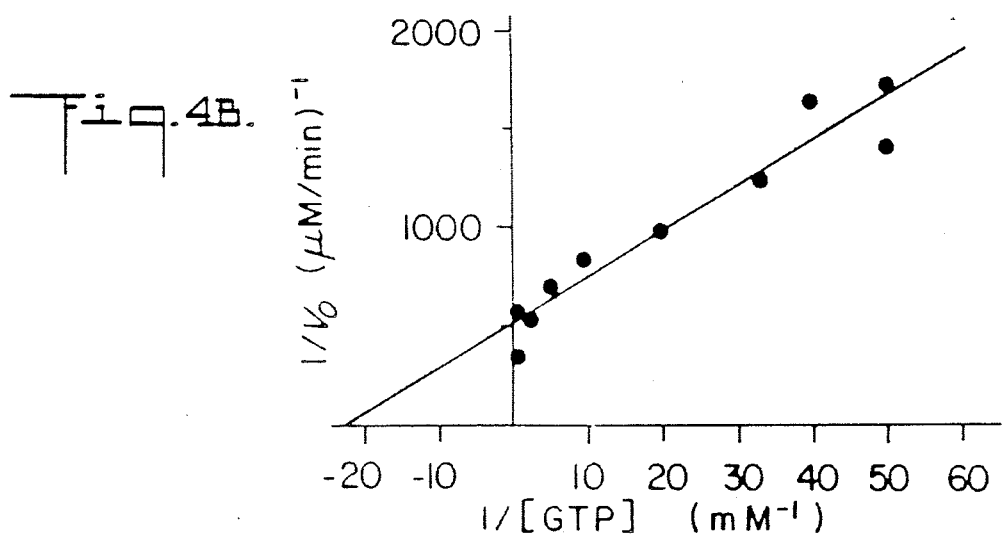

Cleavage is catalytic:

The time course of cleavage of the oligonucleotide substrate GGCCCUCU*AAAAA (where the asterisk designates the cleavage site) by the wild-type ribozyme is shown in FIG. 4a. The reaction of 2.5 uM substrate with 0.2 uM ribozyme is 66% complete in 90 minutes. Thus, it is readily apparent that the ribozyme is acting catalytically.

Figure 4C:
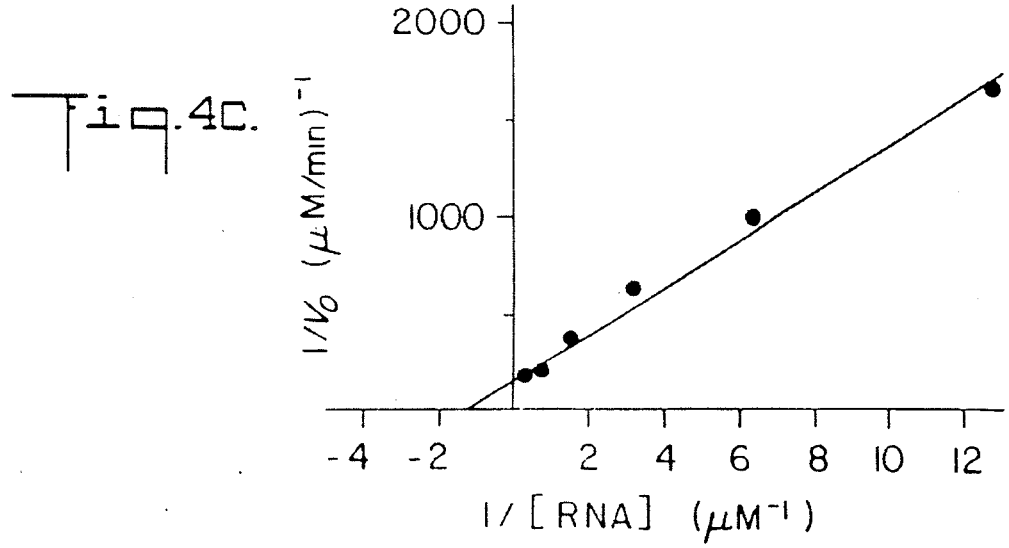

The reaction rate was determined at a series of substrate concentrations. The kinetics are adequately described by the Michaelis-Menten rate law. The dependence of the rate on GTP concentration is shown in the form of a Lineweaver-Burk plot in FIG. 4b. The $K_m$ for GTP is 44 uM. The dependence of the rate on RNA substance concentration at saturating GTP concentration is shown in FIG. 4C. The $K_m$ for this oligoribonucleotide substrate is 0.8 uM, and $k_{cat}$ is 0.13 min$^{-1}$. Thus under Vmax conditions the enzyme turns over about 8 times per hour.

EXAMPLE VII

Figures 5A, 5B:
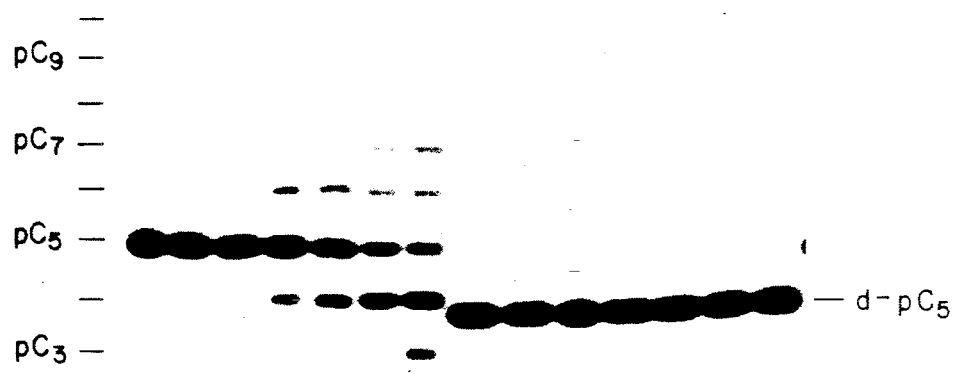
FIG. 5 shows the cleavage and reforming of oligoribonucleotide substrates by L-19 IVS RNA.
Figures 5C, 5D:
Figures 5E, 5F, 5G:
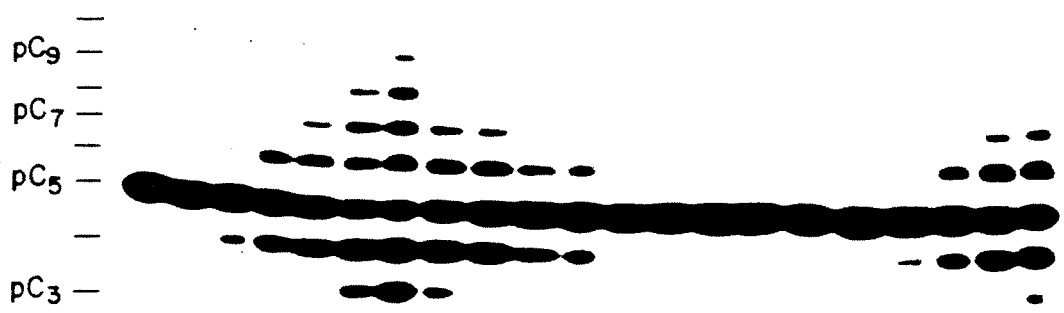

The L-19 IVS RNA catalyzes the cleavage and rejoining of oligonucleotides:

Unlabeled L-19 IVS RNA was incubated with 5'-$^{32}$P-labeled pC$_5$ in a solution containing 20 mM MgCl$_2$, 50 mM tris-HCl, pH 7.5. The pC$_5$ was progressively converted to oligocytidylic acid with both longer and shorter chain length than the starting material (FIG. 5A). The longer products extended to at least pC$_{30}$, as judged by a longer exposure of an autoradiogram such as that shown in FIG. 5A. THe shorter products were exclusively pC$_4$ and pC$_3$. Incubation of pC$_5$ in the absence of the L-19 IVS RNA gave no reaction (FIG. 5C).

Phosphatase treatment of a 60-minute reaction mixture resulted in the complete conversion of the $^{32}$P radioactivity to inorganic phosphate, as judged by polyethyleneimine thin-layer chromatography (TLC) in 1M sodium formate, pH 3.5 (Zaug, A., et al. unpublished data). Thus, the 5'-terminal phosphate of the substrate does not become internalized during the reaction, and the substrate is being extended on its 3' end to form the larger oligonucleotides. When C$_5$p*C was used as the substrate and the products were treated with ribonuclease T$_2$ or ribonuclease A, the $^{32}$P radioactivity was totally converted to Cp* (Zaug, A., et al. unpublished data). Thus, the linkages being formed in the reaction were exclusively 3',5'-phosphodiester bonds. The products of the C$_5$p*C reaction were totally resistant to phosphatase treatment.

The reaction was specific for ribonucleotides, no reaction taking place with d-pC$_5$ (FIG. 1B) or d-pA$_5$ (Zaug, A., et al. unpublished data). Among the oligoribonucleotides, pU$_6$ was a much poorer substrate than pC$_5$ or pC$_6$ (FIG. 5D), and pA$_6$ and gave no reaction (Zaug, A., and Cech, T. R., (1986), Biochemistry 25:4478).

No reaction occurred when magnesium chloride was omitted. The enzyme activity was approximately constant in the range 5 to 40 mM MgCl$_2$ (Zaug, A., et al. unpublished data). The 20 mM concentration was routinely used to circumvent the potential effect of chelation of Mg$^{2+}$ by high concentrations of oligonucleotide substrates.

The L-19 IVS RNA is regenerated after each reaction, such that each enzyme molecule can react with many substrate molecules. For example, quantitation of the data shown in FIG. 5G revealed that 16 pmol of enzyme converted 1080 pmol of pC$_5$ to products in 60 minutes. Such numbers underestimate the turnover number of the enzyme; because the initial products are predominantly C$_6$ and C$_4$, it is likely that the production of chains of length greater than six or less than four involves two or more catalytic cycles. Quantitation of the amount of radioactivity in each product also provides some indication of the reaction mechanism. At early reaction times, the amount of radioactivity (a measure of numbers of chains) in products larger than pC$_5$ is approximately equal to that found in pC$_4$ plus pC$_3$, consistent with a mechanism in which the total number of phosphodiester bonds is conserved in each reaction. As the reaction proceeds, however, the radioactivity distribution shifts toward the smaller products. This is most likely due to a competing hydrolysis reaction also catalyzed by the L-19 IVS RNA, as described below.

The rate of conversion of 30 uM pC$_5$ to products increases linearly with L-19 IVS RNA enzyme concentration in the range 0.06 to 1.00 uM (Zaug, A., et al. unpublished data). At a fixed enzyme concentration (FIG. 5, E to G), there is a hyperbolic relation between the reaction rate and the concentration of pC$_5$. The data are fit by the Michaelis-Menten rate law in FIG. 6. The resulting kinetic parameters are K$_m$=42 uM and k$_{cat}$=1.7 min$^{-1}$.

The stability of the enzyme was determined by preliminary incubation at 42° C. for 1 hour in the presence of Mg$^{2+}$ (standard reaction conditions) or for 18 hours under the same conditions but without Mg$^{2+}$. In both cases, the incubated enzyme had activity indistinguishable from that of untreated enzyme tested in parallel, and no degradation of the enzyme was observed on polyacrylamide gel electrophoresis (Zaug, A., et al. unpublished data). Thus the L-19 IVS RNA is not a good substrate. The enzyme is also stable during storage at −20° C. for periods of months. The specific activity of the enzyme is consistent between preparations.

EXAMPLE VII

Convalent intermediate. When C$_5$p* was used as a substrate, radioactivity became covalently attached to the L-19 IVS RNA (FIG. 7A) (The radioactive phosphate was bonded covalently to the L-19 IVS RNA as judged by the following criteria: it remained associated when the complex was isolated and subjected to a second round of denaturing gel electrophoresis; it was released in the form of a mononucleotide upon RNase T$_2$ treatment; and it was released in the form of a series of unidentified oligonucleotides upon RNase T$_1$ treatment (A. Zaug and T. Cech, unpublished data). These results are consistent with a series of covalent enzyme-substrate complexes in which various portions of C$_5$p*C are linked to the L-19 IVS RNA via a normal 3'-5'-phosphodiester bond. This observation, combined with our previous knowledge of the mechanism of IVS RNA cyclization (Zaug, A. J., et al., (1984) Science 224:574; Sullivan and Cech, T. R., (1985) Cell 42:639; Zaug, A. J., et al. (1983) Nature (London) 301:578), Been, M. and Cech T. R. (1985) Nucleic Acids Res. 13:8389), led to a model for the reaction mechanism involving a covalent enzyme-substrate intermediate (FIG. 8).

This reaction pathway is supported by analysis of reactions in which a trace amount of p*C$_5$ was incubated with a large molar excess of L-19 IVS RNA. The cleavage reaction occurred with high efficiency, as judged by the production of p*C$_4$ and p*C$_3$, but there was very little synthesis of products larger than the starting material (FIG. 7B; compare to FIG. 5A). These data are easily interpreted in terms of the proposed reaction pathway. The first step, formation of the covalent intermediate with release of the 5'-terminal fragment of the oligonucleotide, is occurring normally. The first step consumes all the substrate, leaving insufficient C$_5$ to drive the second transesterification reaction.

The model shown in FIG. 8 was tested by isolating the covalent enzyme-substrate complex prepared by reaction with C$_5$p*C and incubating it with unlabeled C$_5$. A portion of the radioactivity was converted to oligonucleotides with the electrophoretic mobility of C$_6$, C$_7$, C$_8$, and higher oligomers (FIG. 7C). In a confirmatory experiment, the covalent complex was prepared with unlabeled C$_5$ and reacted with p*C$_5$. Radioactivity was again converted to a series of higher molecular weight oligonucleotides (Zaug, A., et al. unpublished data). In both types of experiments the data are readily explained if the covalent complex is a mixture of L-19 IVS RNA's terminating in . . . GpC, . . . GpCpC, . . . GpCpCpC, and so on. Because they can react with C$_5$ to complete the catalytic cycle, these covalent enzyme-substrate complexes are presumptive intermediates in the reaction (FIG. 8). A more detailed analysis of the rate of their formation and resolution is needed to evaluate whether or not they are kinetically competent to be intermediates. We can make no firm conclusion about that portion of the enzyme-substrate complex that did not react with C₅. This unreactive RNA could be a covalent intermediate that was denatured during isolation such that it lost reactivity, or it could represent a small amount of a different enzyme-substrate complex that was nonproductive and therefore accumulated during the reaction.

The $G^{414}$-$A^{16}$ linkage in the C IVS RNA, the $G^{414}$-$U^{20}$ linkage in the C' IVS RNA, and the $G^{414}$-$U^{415}$ linkage in the pre-rRNA are unusual phosphodiester bonds in that they are extremely labile to alkaline hydrolysis, leaving 5' phosphate and 3'-hydroxyl termini (Zaug, A. J. et al, (1984) Science 224:574 and Inoue, T., et al. (1986) J. Mol. Biol. 189,143–165). We therefore tested the lability of the $G^{414}$-C linkage in the covalent enzyme-substrate intermediate by incubation at pH 9.0 in a $Mg^{2+}$-containing buffer. This treatment resulted in the release of products that comigrated with pC and pCpC markers and larger products that were presumably higher oligomers of pC (FIG. 7D). Thin-layer chromatography was used to confirm the identity of the major products (Zaug, A., et al. unpublished data). In those molecules that released pC, the release was essentially complete in 5 minutes. Approximately half of the covalent complex was resistant to the pH 9.0 treatment. Once again, we can make no firm conclusion about the molecules that did not react. The lability of the $G^{414}$-C bond forms the basis for the L-19 IVS RNA acting as a ribonuclease (FIG. 8) by a mechanism that is distinct from that of the endoribonuclease described in Examples I through VI.

A competitive inhibitor. Deoxy C₅, which is not a substrate for L-19 IVS RNA-catalyzed cleavage, inhibits the cleavage of pC₅ (FIG. 9A). Analysis of the rate of the conversion of pC₅ to pC₄ and pC₃ as a function of d-C₅ concentration is summarized in FIG. 9B and C. The data indicate that d-C₅ is a true competitive inhibitor with the inhibition constant $K_i$=260 uM. At 500 uM, d-A₅ inhibits the reaction only 16 percent as much as d-C₅. Thus, inhibition by d-C₅ is not some general effect of introducing a deoxyoligonucleotide into the system but depends on sequence.

The formation of the covalent enzyme-substrate intermediate (EpC) can be represented as

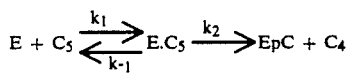

If $k_{-1} >> k_2$, then $K_m = k_{-1}/k_1$, the dissociation constant for the noncovalent E·C₅ complex. The observation the the $K_i$ for d-C₅ is within an order of magnitude of the $K_m$ for C₅ can then be interpreted in terms of d-C₅ and C₅ having similar binding constants for interaction with the active site on the enzyme. This fits well with the idea that the substrate binds to an oligopurine (R₅) sequence in the active site primarily by Watson-Crick base-pairing, in which case the C₅·R₅ duplex and the d-C₅·R₅ duplex should have similar stability.

Enzyme mechanism and its relation to self-splicing. The stoichiometry of the reaction products (equimolar production of oligonucleotides smaller than and larger than the starting material), the lack of an ATP or GTP (adenosine triphosphate; guanosine triphosphate) energy requirement, the involvement of a covalent intermediate, the specificity for oligoC substrates, and the competitive inhibition by d-C₅ lead to a model for the enzyme mechanism (FIG. 8). The L-19 IVS RNA is proposed to bind the substrate noncovalently by hydrogen-bonded base-pairing interactions. A transesterification reaction between the 3'-terminal guanosine residue of the enzyme and a phosphate ester of the substrate then produces a covalent enzyme-substrate intermediate.

Transesterification is expected to be highly reversible. If the product C₄ rebinds to the enzyme, it can attack the covalent intermediate and reform the starting material, C₅. Early in the reaction, however, the concentration of C₅ is much greater than the concentration of C₄; if C₅ binds and attacks the covalent intermediate, C₆ is produced (FIG. 8). The net reaction is 2 C₅ converted to C₆+C₄. The products are substrates for further reaction, for example, C₆+C₅ is converted to C₇+C₄ and C₄+C₅ is converted to C₃+C₆. The absence of products smaller than C₃ is explicable in terms of the loss of binding interactions of C₃ relative to C₄ (C₃ could form only two base pairs in the binding mode that would be productive for cleavage).

The transesterification reactions are conservative with respect to the number of phosphodiester bonds in the system. Thus, RNA ligation can occur without an external energy source as is required by RNA or DNA ligase. Hydrolysis of the covalent intermediate competes with transesterification. The net reaction is C₅+H₂O converted to C₄+pC, with the L-19 IVS RNA acting as a ribonuclease.

On the basis of our current understanding of the reaction, the catalytic strategies of the L-19 IVS RNA enzyme appear to be the same as those used by protein enzymes (Jencks, W. P., (1969) Catalysis in Chemistry and Enzymology (McGraw-Hill, New York). First, the RNA enzyme, like protein enzymes, forms a specific noncovalent complex with its oligonucleotide substrate. This interaction is proposed to hold the oligonucleotide substrate at a distance and in an orientation such as to facilitate attack by the 3'-hydroxyl of the terminal guanosine of the enzyme. Second, a covalent enzyme-substrate complex is a presumptive intermediate in the L-19 IVS RNA reaction. Covalent intermediates are prevalent in enzyme-catalyzed group transfer reactions. Third, the phosphodiester bond formed in the covalent intermediate is unusually susceptible to hydrolysis, suggesting that it may be strained or activated to facilitate formation of the pentavalent transition state upon nucleophilic attack (Zaug, A. J., et al. (1985) Biochemistry 24:6211; Zaug, A. J., et al. (1984) Science 224:574). Similarly, protein catalysts are thought to facilitate the formation of the transition state, for example, by providing active site groups that bind the transition state better than the unreacted substrate (Fersht, A., (1985) Enzyme Structure and Mechanism (Freeman, New York, ed. 2); Wells, T.N.C., et al. (1985) Nature (London) 316:656). Thus far there is no evidence that another major category of enzyme catalysis, general acid-base catalysis, occurs in the L-19 IVS RNA reactions, but we think it likely that it will be involved in facilitating the required proton transfers.

Each L-19 IVS RNA-catalyzed transesterification and hydrolysis reaction is analogous to one of the steps in Tetrahymena pre-rRNA self-splicing or one of the related self-reactions (FIG. 10). Thus, the finding of enzymatic activity in a portion of the IVS RNA validates the view that the pre-rRNA carries its own splicing enzyme as an intrinsic part of its polynucleotide chain. It seems likely that the C₅ substrate binding site of the L-19 IVS RNA is the oligopyrimidine binding site that directs the choice of the 5' splice site and the various IVS RNA cyclization sites (Sullivan, F. X., et al. (1985) Cell Supra; Been, M., et al. (1985) Nucleic Acid Research Supra; Inoue, T., et al. J. Mol. Biol., Supra; Inoue, T., et al. (1985) Cell 43:431. Although the location of this site within the IVS RNA has not been proved, the best candidate is a portion of the "internal guide sequence" proposed by Davies and co-workers (Davies, R. W., et al. (1982) Nature (London) 300:719; Waring, R. B., et al. (1983) J. Mol. Biol. 167:595). Michel and Dujon (Michel, F., et al. (1983) EMBO J. 2:33) show a similar pairing interaction in their RNA structure model. The putative binding site, GGAGGG, is located at nucleotides 22 to 27 of the intact Tetrahymena IVS RNA and at positions 3 to 8 very near the 5' end of the L-19 IVS RNA. If this is the substrate binding site, site-specific mutation of the sequence should change the substrate specificity of the enzyme in a predictable manner.

EXAMPLE IX

The L-19 IVS RNA Dephosphorylates $C_6p$. When oligo(cytidylic acid) with a 3'-terminal hydroxyl group is incubated with the L-19 IVS RNA enzyme in 20 mM $MgCl_2$, it is converted to oligo(C) with both larger and smaller chain lengths (FIG. 1A) as described previously (Examples VII and VIII and Zaug & Cech, (1986) Science (Wash., D.C.) 231:470-475. The reaction is specific for oligo(C); for example, $pA_6$—OH is unreactive under the same conditions (FIG. 11A).

When oligo(cytidylic acid) with a 3'-terminal phosphate is incubated with excess L-19 IVS RNA in 20 mM $MgCl_2$, the substrate is converted to a product with reduced electrophoretic mobility (FIG. 11A). This abrupt reduction in electrophoretic mobility, equivalent to an increase of approximately three nucleotides on a sequencing ladder, is exactly that obtained by treating the substrate with alkaline phosphatase (not shown in FIG. 11; an example is shown in FIG. 12). Thus, it appeared that the product was $C_6$—OH. When the substrate is internally labeled ($C_5p^*Cp$), the labeled phosphate is retained in the product (FIG. 11A). On the other hand, when the substrate is terminally labeled ($C_5p^*$), the oligonucleotide product is unlabeled and the L-19 IVS RNA becomes labeled (FIG. 11B). These findings confirmed that the reaction involves removal of the 3'-terminal phosphate of the substrate.

Dephosphorylation is specific for the 3'-phosphate of oligo(cytidylic acid). The 5'-phosphate of $pC_5$ is not reactive (FIG. 11A), and neither phosphate is removed from pCp (data not shown). (We estimate that 0.1% reaction would have been detected). Neither $A_6Cp$ (FIG. 11A) nor $pA_6p$ (not shown) is a substrate. (We estimate that 0.1% reaction would have been detected). On the basis of this sample, it appears that there is both a minimum length requirement and a sequence requirements for a substrate and that the requirement are similar to those of the nucleotidyl transfer activity of the L-19 IVS RNA (Zaug & Cech, (1986) Science Supra).

EXAMPLE X

Formation and Stability of E-p. We next investigated the fate of the phosphate that is removed from $C_5p$ in the presence of L-19 IVS RNA. At neutral pH no inorganic phosphate is formed during the reaction, as judged by thin-layer chromatography of the reaction products (data not shown). When the reaction is conducted in the presence of $C_5p^*$, it becomes clear that the phosphate is transferred to the L-19 RNA (FIG. 11B). Treatment of the phosphorylated L-19 IVS RNA (hereafter called E-p) with alkaline phosphatase leads to quantitative release of the radioactivity in the form of inorganic phosphate. Thus, the dephosphorylation of the substrate is accomplished by transphosphorylation. The structure of E-p has been determined; the phosphate is esterified through the 3'-0 of the 3'-terminal guanosine residue (G414) of the RNA (Zaug and Cech, unpublished results).

The rate of conversion of $G_5p$ to $C_5$—OH+E-p is pH-dependent with an optimum around pH 5.0. A sample of the data is shown in FIG. 12. The phospho transfer reaction is essentially pH-independent in the range pH 7.5-9 and proceeds at a rate similar to that of the nucleotidyl transfer reaction (FIG. 12A). At pH 5 the phospho transfer reaction is accelerated more than 20-fold, while the nucleotidyl transfer reaction is unaffected. At pH 4, the enzyme still has substantial phospho transfer activity while its nucleotidyl transfer activity is greatly diminished. Since the enzyme is probably starting to denature below pH 5 (Zaug, et al., (1985) Biochemistry 24:6211) the phospho transfer activity profile in this range presumably reflects the inactivation of the enzyme rather than the pH optimum for the transfer step. Data such as those shown in FIG. 12B were quantified, and the resulting rate constants are summarized in FIG. 12C.

The covalent intermediate formed during the reaction of $pC_5$—OH with the L-19 IVS RNA (E-pC) is alkali-labile; at pH 9.0 it undergoes hydrolysis, releasing the nucleotide pC and regenerating the free enzyme (Zaug & Cech, (1986) Science Supra). We therefore investigated the stability of the phosphate monoester in the phosphenzyme E-p. There is no detectable hydrolysis of the phosphate monoester at pH 9.0, conditions in which E-pC treated in parallel gave release of pC, or at any other pH in the range 7.0-9.0.

At acidic pH, on the other hand, the terminal phosphate monoester of E-p underwent slow hydrolysis. When E-p was incubated at pH 5.0, the phosphate was released as $P_i$ at a rate of approximately 10%/h. The rate was slower at pH 4.0 and at pH 6.0 than at pH 5.0. Release of $P_i$ was also observed during the reaction of $C_5p^*$ with L-19 IVS RNA at pH 5.0 at reaction times of 2 and 4h. Thus, the L-19 IVS RNA has acid phosphatase activity. This hydrolytic reaction is so slow, however, that we have not attempted to demonstrate multiple turnover.

EXAMPLE XI

Phosphorylation of the Enzyme Is Reversible. When unlabeled E-p is incubated with a trace amount of $C_5p^*$, very little reaction takes place (FIG. 13A). In contrast, when the same E-p is incubated with a trace amount of labeled $pC_5$—OH, labeled pCsp is progressively formed (FIG. 13B). The products normally formed by incubation of $pC_5$—OH with excess L-19 IVS RNA, $pC_4$—OH and $pC_3$—OH (Zaug & Cech, 1986), are not observed. Thus, E-p is inactive as a nucleotidyltransferase but is readily subject to a reverse phosphorylation reaction.

The reversibility of phosphorylation of the L-19 IVS RNA was confirmed by reacting the enzyme with $C_5p^*$ to form E-p*, purifying the E-p*, and incubating it with unlabeled $C_5$—OH. A labeled product corresponding to $C_5p^*$ was produced (data not shown). This approach allowed to rapid screening of a series of nucleotides and oligonucleotides for their ability to reverse the phosphorylation reaction. As shown in Table 2, of the oligonucleotides tested only UCU and C4U had activity comparable to the of C5. It remains possible that some of the other oligonucleotides have a high $K_m$ and would have detectable activity at a higher concentration.

EXAMPLE XII

Figure 14A:
FIG. 14 shows the L-19 IVS RNA acts catalytically as a phosphotransferase.
Figure 14B:
Figure 14C:
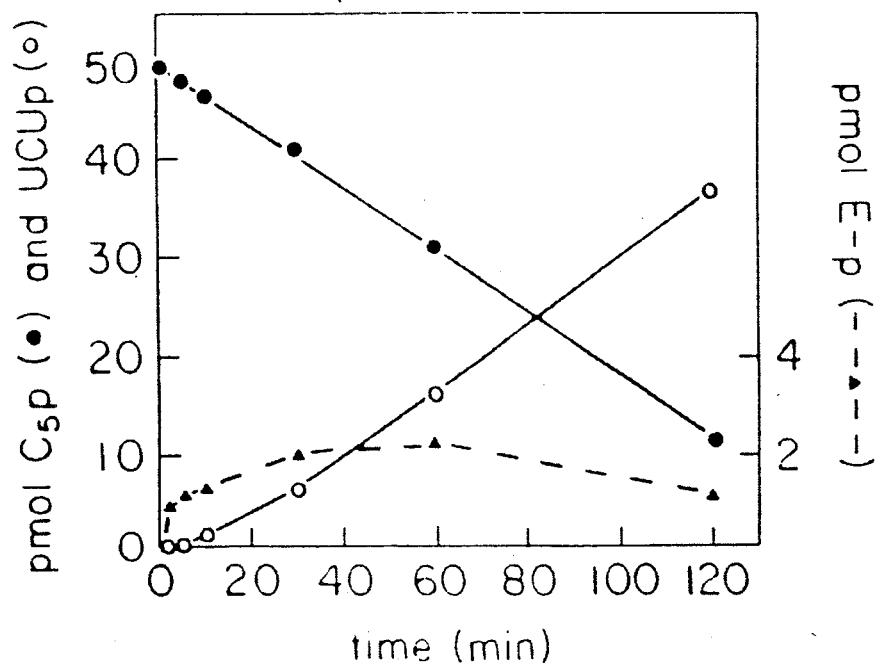

The L-19 IVS RNA Is a Phosphotransferase. The phosphotransfer reactions described thus far were all done in enzyme excess. To prove that the L-19 IVS RNA could act catalytically, it was necessary to show that each enzyme molecule could mediate the dephosphorylation of multiple substrate molecules. This was accomplished by the incubation of L-19 IVS RNA with a molar excess of C5p* and an even greater molar excess of unlabeled UCU, to act as a phosphate acceptor. As shown in FIG. 14A, L-19 IVS RNA was capable of transferring the 3'-terminal phosphate from C5p to UCU. Treatment of the product with RNase T2 and thin-layer chromatography confirmed that the phosphate had been transferred from a C to a U residue. The time course in FIG. 14B was done under conditions of lower enzyme concentration (0.16 uM) and higher acceptor concentration (200 uM) than those used in the experiment of FIG. 14A. Quantitation of the data (FIG. 14C) showed that under these conditions 11 substrate molecules were dephosphorylated per enzyme molecule after 120 min. Phosphorylation of the enzyme precedes substantial product formation, consistent with E-p being an oligatory intermediate in the reaction. At steady state 63% of the enzyme is present as E-p.

EXAMPLE XIII

Plasmid Construction

Been, Michael D. and Cech, Thomas, R. (1986) Cell 47:207-216 reports the construction of the pBG plasmid series. In general, the plasmid used for these studies (pBGST7) was derived from the cloning vector pUC18. The methodology for the following manipulations is described in Maniatis, T., et al. (1982) Molecular Cloning: A Laboratory Manual (Cold Spring Harbor, N.Y.: Cold Spring Harbor). pUC18 was partially digested with HaeII and unit length linear molecules were isolated by agarose gel electrophoresis and electroelution. The recovered DNA was treated with T4 DNA polymerase to make blunt ends and then dephosphorylated with calf intestinal phosphatase. pT7-2 (U.S. Biochemical Corp.) was cut with PvuII and HindIII and treated with T4 DNA polymerase, and the fragment containing the phage T7 promoter was isolated by polyacrylamide gel electrophoresis and electroelution. The promoter-containing fragment was ligated into the linearized pUC18 and the plasmid transformed into E. coli strain JM83. Individual colonies were picked and miniprep DNA was screened by restriction endonuclease digestion to locate the promoter fragment to the correct HaeII site (position 680 on the map in the New England Biolabs Catalog). The orientation of the T7 promoter was determined by transcribing EcoRI-cut miniprep DNA with T7 RNA polymerase and determining the size of the product. This plasmid (pUT718) was then cut in the multicloning site with KpnI and SphI and treated with T4 DNA polymerase followed by calf intestinal phosphatase. An IVS-containing BamHI DNA fragment was isolated from pJE457 (Price, J. V. and Cech, T. R., (1985) Science 228:719-722) and treated with S1 nuclease, phenol extracted, chloroform extracted, and ethanol precipitated. The S1-treated fragment, containing short deletions at both ends, was ligated into the KpnI/SphI-cut pUT718. E. coli strain JM83 was transformed with the recombinant plasmid and plated on LB agar containing ampicillin and X-gal (5-bromo-4-chloro-3-indolyl-beta-D-galactoside). DNA isolated from blue colonies was assayed by agarose gels electrophoresis for IVS-size inserts. Exon sequences were determined by dideoxy-sequencing the miniprep DNA. Ideally, only plasmids containing IVS and exons that will preserve the reading frame of the lacZ gene fragment should give blue colonies and this will depend on the splicing of the message in E. coli (Waring, R. B., et al, (1985) Cell 40:371-380; Price, J. V. and Cech, T. R., (1985) Science 228:719-722). In fact, several plasmids that conferred a light blue color to the colonies had exons for which correct splicing of the IVS should not generate the proper reading frame; these were not investigated further. One that produced a dark blue colony, pBGST7 (FIG. 16), also had the expected reading frame and was used for these studies.

Mutagenesis

Oligonucleotide-directed mutagenesis on plasmid DNA was done essentially as described by Inouye, S. and Inouye M. (1986) In DNA and RNA Synthesis, S. Narang, ed. (New York: Academic Press), in press. pBGST7 DNA was cleaved in the gene coding for ampicillin resistance with XmnI. In a separate reaction, pBGST7 DNA was cut with EcoRI and HindIII, sites that flank the IVS and exon sequences. The vector portion of the plasmid was separated from the IVS-containing fragment by agarose gel electrophoresis and recovered by electroelution. XmnI-cut DNA was mixed with the vector fragment in the presence of the oligonucleotide containing the mismatched base, heated to 95° C. for 5 min, placed at 37° C. for 30 min, then at 4° C. for 30 min and then put on ice. The products were treated with dNTPs and Klenow fragment of DNA pol I at room temperature for 2 hr. E. coli strain JM83 was transformed with the DNA and ampicillin-resistant colonies were picked on the basis of color (white or light blue indicating loss of splicing activity) and the miniprep DNA was sequenced.

The double mutants were made using the plasmid DNA of single mutants and screening for restored beta-galactosidase activity. pBG/-2G:23C was made from pBG/-2G and a second oligonucleotide directed at position 23. pBG/-3G:24C was made starting with pBG/24C and using the oligonucleotide directed at position −3. pBG/-4G:25C was made by generating a circular heteroduplex from pBG/-4G:25C that had been linearized at different positions. Transformation of these heteroduplexes generated blue and light blue colonies, both at a low frequency. The blue colonies were wild-type sequence the light blues double mutant.

pSPTT1A3:

The ThaI fragment of Tetrahymena ribosomal RNA gene contains the IVS and small portions of the flanking exons. Hind III linkers were ligated onto the ends of the ThaI fragment and it was inserted into the Hind III site in the polylinker of pSP62 (New England Nuclear), which contains the SP6 promoter. The recombinant plasmid was cloned in E. coli by standard methods.

pT7TT1A3:

Construction of pT7TT1A3 was identical to pSPTT1A3 except that the ThaI fragment was cloned into the Hind III site of pT7-2 (U.S. Biochemical Corp.) which contains the T7 promoter.

pT7 L-21 plasmid:

pBGST7 (described in Been & Cech, (1986) Cell 47:207 was cleaved with restriction endonucleases SphI and Hind III and the small fragment containing the IVS minus its first 44 nucleotides was purified. pUC18 was cleaved with SpH I and Hind III, mixed with the Sph-HIND III fragment from pBGST7 and treated with DNA ligase. *E. coli* cells were transformed, colonies were picked, plasmid DNA was isolated from individual colonies and sequenced. A plasmid containing the SphI-Hind III fragment of the IVS properly inserted into pUC18 was selected for the next step. This plasmid was cleaved with SphI and EcoRI restriction endonucleases and a synthetic oligonucleotide was inserted into the plasmid using DNA ligase. The synthetic oligonucleotide contained one-half of the EcoRI restriction site, the T7 promoter, and nucleotides 22-44 of the Tetrahymena IVS, ending at the SphI site. *E coli* cells were transformed, colonies were picked, plasmid DNA was isolated from individual colonies and sequenced.

The final plasmid pT7L-21 was found by sequence analysis to contain the T7 promoter properly juxtaposed to nucleotide 22 of the IVS. (See FIG. 16)

Therefore the method can be used to create defined pieces of RNA. For example, these defined pieces can be 5'—OH or 3'—OH end pieces, or center pieces containing the active site for study and production of varient RNA forms.

TABLE 1

Sites of cleavage of large RNA substrates by the wild-type L - 19 $IVS_\beta$ RNA.

| Substrate | Site | Size (nt)* | Sequence+ | |
|---|---|---|---|---|
| pAK-105 ($\beta$-globin pre-mRNA) | 1 | 148 | −6 UCCUCU ↓ | −1 GCCUC |
| | 2 | 464 | AACUCU | AAGAG |
| pT7-1 (pBR322) | 1 | 145 | UCCCUU | UUUUG |
| | 2 | 556 | CACUCU | CAGUA |
| | 3 | 603 | UAUUUU | CUCCU |
| | 4 | 805 | UCCUCU | AGAGU |
| Consensus observed | | | $U_A^C$CUCU ↓N | |
| expected | | | $C_U^C$CUCU ↓N | |

*Size of the GTP-labeled fragment.
+Sequences are listed in 5'→3' direction. Arrows indicate sites of cleavage and guanosine addition.

The expected consensus sequence is based on the known sequence at the end of the 5' exon (CUCUCU) modified by the possibility that either a C or a U at position −5 might be able to pair with the G in the active site. At position −1, there is some basis for thinking that a C might not be as good as a U (Davies, R.W., et al. (1982) Nature 300:710-724; Michel, F., et al. (1983) EMBO J. 2:33-38; Inoue, T., et al. (1986) J. Mol. Biol. 189:143-165.

TABLE 2

Relative Activity of Different Acceptors in the Transphosphorylation Reaction$^a$

| acceptor | activity |
|---|---|
| UTP | − |
| CTP | − |
| UC | − |
| CC | − |
| AA | − |
| GU | − |

TABLE 2-continued

Relative Activity of Different Acceptors in the Transphosphorylation Reaction$^a$

| acceptor | activity |
|---|---|
| UU | − |
| CU | − |
| AUU | − |
| UUU | − |
| UCU | ++ |
| CCU | +/− |
| $AU_3$ | − |
| $GU_3$ | − |
| $C_4U$ | ++ |
| $C_5$ | ++ |
| $U_6$ | +/− |
| $dC_5$ | − |

$^a$E-p* was incubated with 10 $\mu$M oligonucleotide (or mono- or di-nucleotide) in 20 mM $MgCl_2$ and 50 mM Tris-HCl, pH 7.5, at 42° C. for 30 min. Transfer of the phosphate to the oligonucleotide was assayed by sequencing gel electrophoresis and autoradiography. ++, approximately the same activity as $C_5$; +/−, barely detectable activity, estimated as ~1% that of $C_5$; −, no activity detectable under these conditions.

What is claimed:

1. Method for dephosphorylation of an RNA substrate comprising the steps of:
   providing an enzymatic RNA molecule having a dephosphorylation activity independent of any protein, and
   contacting said enzymatic RNA molecule with said RNA substrate under conditions suitable for said enzymatic RNA molecule to remove the 3' terminal phosphate of said RNA substrate.

2. A method for locating a nucleotide sequence in an RNA molecule having a first length, comprising the steps of:
   providing an enzymatic RNA molecule having an endonuclease activity independent of any protein,
   contacting said enzymatic RNA molecule with said RNA molecule wherein said enzymatic RNA molecule will cleave said RNA molecule at any said nucleotide sequence present in said RNA molecule, and
   determining the length of resulting RNA molecules resulting from said contacting step as an indication of the location of the nucleotide sequence in said RNA molecule.

3. A method for locating a plurality of nucleotide sequences in an RNA molecule having a first length, comprising the steps of:
   providing a plurality of different enzymatic RNA molecules having an endonuclease activity independent of any protein, each said different enzymatic RNA molecule cleaving said RNA molecule at a different said nucleotide sequence of said plurality of nucleotide sequences;
   contacting said plurality of different enzymatic RNA molecules with said RNA molecule wherein each said different enzymatic RNA molecule will cleave said RNA molecule at any said different nucleotide sequence present in said RNA molecule, and
   determining the length of resulting RNA molecules resulting from said contacting step as an indication of the location of the nucleotide sequence in said RNA molecule.

4. A method for detecting the presence of a nucleotide sequence in an RNA molecule, comprising the steps of:
   providing an enzymatic RNA molecule having an endonuclease activity independent of any protein, contacting said enzymatic RNA molecule with said RNA molecule wherein said enzymatic RNA molecule will cleave said RNA molecule of any said nucleotide sequence present in said RNA molecule to produce two or more fragments of said RNA molecule, and detecting the presence of said fragments as an indication of the presence of said nucleotide sequence.

5. Method of claim 2, 3 or 4 wherein a radiolabelled guanosine derivative is provided in said contacting step to cause radiolabelling of the 5' end of any cleaved said RNA molecule.

6. Method for producing an enzymatic RNA molecule having an endonuclease activity independent of any protein, comprising the steps of:
   (a) transcribing recombinant DNA encoding a precursor RNA molecule to said enzymatic RNA molecule with an RNA polymerase in vitro to produce said precursor RNA;
   (b) incubating said precursor RNA under conditions suitable for promoting self-splicing and cyclization of said precursor RNA to produce cyclized RNA;
   (c) contacting said cyclized RNA with $MgCl_2$ at pH 9.0 to promote conversion of said cyclized RNA to said enzymatic RNA molecule; and
   (d) purifying said enzymatic RNA molecule by polyacrylamide gel electrophoresis and chromatography.

7. Method of claim 6 wherein said recombinant DNA is cloned in *E. coli*.

8. Method of claim 6 wherein said recombinant DNA comprises an intron of a Tetrahymena gene encoding ribosomal RNA.

9. Method of claim 6 wherein the expression of said DNA is regulated by the SP6 or T7 RNA polymerase promoter.

10. A method for producing an enzymatic RNA molecule having an endonuclease activity of any protein, comprising the steps of:
   providing DNA encoding RNA consisting essentially of said enzymatic RNA molecule under the transcriptional control of a promoter, and
   transcribing said DNA from said promoter to produce said enzymatic RNA molecule.

11. A vector for production of an enzymatic RNA molecule having an endonuclease activity independent of any protein, comprising:
   DNA encoding said enzymatic RNA molecule, and
   a promoter positioned relative to said DNA to cause transcription of said DNA to form an RNA molecule consisting essentially of said enzymatic RNA molecule.

12. The vector of claim 11 wherein said endonuclease activity is specific for a nucleotide sequence defining a cleavage site comprising single stranded RNA in a separate RNA molecule and causing cleavage at said cleavage site by a transesterification reaction.

13. The vector of claim 11 wherein said endonuclease activity is specific for a nucleotide sequence defining a cleavage site consisting essentially of a single stranded region of a separate RNA molecule.

14. The vector of claim 11 or 13 wherein the nucleotide sequence defining said cleavage site comprises four or more bases.

15. The vector of claim 13 wherein said endonuclease activity causes cleavage at said cleavage site by a transesterification reaction.

16. The vector of claim 11 wherein said enzymatic RNA molecule comprises an active site region responsible for said cleavage substantially identical to the active site region of the ribosomal RNA intervening sequence naturally occurring in Tetrahymena.

17. The vector of claim 16 wherein said nucleotide sequence defining said cleavage site is chosen from GUCU, CUGU, and CGCU.

18. The vector of claim 11 wherein said enzymatic RNA molecule has a pH optimum for said endonuclease activity between 7.5 and 8.

19. The vector of claim 11 wherein said endonuclease activity requires the presence of magnesium ions, a denaturant, or a guanine derivative.

20. The vector of claim 11 wherein said endonuclease activity is enhanced by the presence of a divalent cation.

21. The vector of claim 20 wherein said divalent cation is magnesium.

22. The vector of claim 11 wherein said enzymatic RNA molecule further comprises a second endonuclease activity, independent of any protein, for nucleic acid comprising deoxyribonucleotides wherein said endonuclease activity and said second endonuclease activity may be the same or different.

23. The vector of claim 11 wherein said enzymatic RNA molecule further has a nucleotidyl transferase activity.

24. The vector of claim 23 wherein said nucleotidyl transferase activity causes polymerization of oligocytidylic acid to polycytidylic acid.

25. The vector of claim 11 wherein said enzymatic RNA molecule further has a dephosphorylase activity.

26. The vector of claim 25 wherein said dephosphorylase activity causes removal of a 3' terminal phosphate of a nucleic acid comprising a 3' ribonucleotide.

27. The vector of claim 26 wherein said dephosphorylase activity is specific to a specific nucleotide sequence.

28. The vector of claim 11 wherein said enzymatic RNA molecule comprises the ribonucleotide base sequence of L-19 RNA, said enzymatic RNA molecule having a ribonucleotide base sequence at the active site responsible for said cleavage different from that of L-19 from Tetrahymena.

29. The vector of claim 11 wherein said enzymatic RNA molecule comprises the ribonucleotide base sequence of L-19 RNA.

30. The vector of claim 29 wherein said L-19 comprises bases 19–331 of Tetrahymena L-IVS.

31. The vector of claim 11 wherein said activity causes cleavage of a separate RNA molecule at a specific nucleotide sequence defining a cleavage site comprising single stranded RNA in a separate RNA molecule, said enzymatic RNA molecule not causing specific cleavage of said separate RNA molecule immediately adjacent in the direction 3' to the nucleotide sequence CUCU.

32. The vector of claim 11, said vector being a plasmid.

33. The vector of claim 11 wherein said promoter is selected from the group consisting of the bacteriophage SP6 and bacteriophage T7 promoters.

34. The vector of claim 11, wherein said enzymatic RNA molecule comprises bases 21–331 of Tetrahymena L-IVS.

35. A plasmid selected from the group consisting of pSPTT1A3, pT7-TT1A3, pBGST7, pBG/-2G:23C, pBG/23C, pBG/-3G:24C, pBG/24C, pBG/-4G:25C, pBG/25C, and pBG/23A$_4$.

* * * * *